United States Patent
Yamauchi et al.

(10) Patent No.: US 7,416,623 B2
(45) Date of Patent: Aug. 26, 2008

(54) METHOD OF CAUSING INTERGRANULAR STRESS CORROSION CRACK TO GENERATE AND GROW IN SAMPLE

(75) Inventors: Kiyoshi Yamauchi, Kure (JP); Fumio Manabe, Kure (JP)

(73) Assignee: Babcock-Hitachi K.K., Tokyo (JP)

( * ) Notice: Subject to any disclaimer, the term of this patent is extended or adjusted under 35 U.S.C. 154(b) by 396 days.

(21) Appl. No.: 10/512,423

(22) PCT Filed: Apr. 25, 2003

(86) PCT No.: PCT/JP03/05400

§ 371 (c)(1), (2), (4) Date: Jan. 26, 2005

(87) PCT Pub. No.: WO03/091709

PCT Pub. Date: Nov. 6, 2003

(65) Prior Publication Data

US 2005/0167014 A1    Aug. 4, 2005

(30) Foreign Application Priority Data

Apr. 26, 2002   (JP) ............................. 2002-127234

(51) Int. Cl.
*C21D 1/68* (2006.01)
(52) U.S. Cl. ...................... 148/636; 148/713
(58) Field of Classification Search ................. 148/519, 148/527, 713
See application file for complete search history.

(56) References Cited

U.S. PATENT DOCUMENTS

| | | | | |
|---|---|---|---|---|
| 3,378,411 A | * | 4/1968 | Bergen | 148/276 |
| 3,785,787 A | | 1/1974 | Yokota et al. | |
| 4,275,414 A | * | 6/1981 | Norris | 348/83 |
| 4,596,142 A | * | 6/1986 | Poole et al. | 73/579 |
| 4,779,453 A | * | 10/1988 | Hopenfeld | 73/86 |
| 5,178,822 A | * | 1/1993 | Buford et al. | 376/305 |
| 5,789,720 A | * | 8/1998 | LaGally et al. | 219/121.64 |

FOREIGN PATENT DOCUMENTS

| | | |
|---|---|---|
| JP | 9-54061 A | 2/1997 |
| JP | 11-132921 A | 5/1999 |

(Continued)

OTHER PUBLICATIONS

S. Ahmad et al., Stress Corrosion Cracking of Sensitized 304 Austenitic Stainless Steel in Petroleum Refinery Environment., National Association of Corrosion Engineers, vol. 38, No. 6, pp. 347-353, Jun. 1982.

(Continued)

*Primary Examiner*—George Wyszomierski
(74) *Attorney, Agent, or Firm*—Crowell & Moring LLP

(57) ABSTRACT

To provide a method for simply and easily causing only IGSCC to initiate and grow in a specimen, which can retain corrosion resistance through passivation, under atmospheric pressure in a short time, an aqueous solution of potassium tetrathionate is brought into contact with the specimen capable of retaining corrosion resistance through passivation. The potassium tetrathionate concentration, temperature and pH value of the aqueous solution are from 0.3 to 6 wt. %, from 5 to 60° C., and from 3 to 6, respectively.

4 Claims, 49 Drawing Sheets

FOREIGN PATENT DOCUMENTS

| | | |
|---|---|---|
| JP | 2001-99812 A | 4/2001 |
| JP | 2001-141878 A | 5/2001 |
| JP | 2002-333397 A | 11/2002 |

OTHER PUBLICATIONS

K. Hosoya et al., IGSCC Susceptibility of Austenitic Stainless Steels in Acidified $K_2S_4O_6$ Solution—New Polythionic Acid SCC Test Solution—Corrosion Engineering, vol. 34, No. 10, pp. 568-572, Oct. 1985.

K. Yamauchi et al., Improvement of Intergranular Corrosion and Intergranular Stress Corrosion Cracking Resistance of Nickel-base Weld Metals by Stabilization Parameter Control. Corrosion Engineering, vol. 35, No. 11, pp. 605-615, 1986.

M.E. Indig et al., High Temperature Electrochemical Studies of Stress Corrosion of Type 304 Stainless Steel. Corrosion-Nace, vol. 35 No. 7, pp. 288-295, 1979.

R.M. Chrenko. Residual Stress Measurements on Type 304 Stainless Steel Welded Pipes. May 1980. NTIS, order No. DE82900053. Seminar on Countermeasures for Pipe Cracking in BWRs; Palo Alto, Ca. pp. 1-22.

G. Buzzanca et al., A Contribution to the Interpretation of the Strain Rate Effect on Type 304 Stainless Steel Intergranular Stress Corrosion Cracking. Corrosion Science, vol. 25, No. 8/9, pp. 805-813. 1985.

Spanish Search Report dated Sep. 10, 2007 (Four (4) pages).

\* cited by examiner

FIG. 3

| Material | C | Si | Mn | P | S | Ni | Cr | Fe | Nb | Ti |
|---|---|---|---|---|---|---|---|---|---|---|
| Alloy 182 | 0.041 | 0.2 | 3.03 | 0.005 | 0.0030 | 70.5 | 14.45 | 9.53 | 1.69 | <0.3 |
| Alloy 600 | 0.06 | 0.32 | 0.36 | 0.004 | 0.0009 | 76.67 | 15.86 | 6.41 | <0.1 | <0.3 |

| Test conditions | Test solution designation | Surrounding water | Pressure (MPa) | Solution temperature (°C) | Load strain (%) |
|---|---|---|---|---|---|
| Invention | A | 1% K₂S₄O₆ | Atmospheric pressure | RT | 1.5 |
| Comparative conditions | B | 1% K₂S₄O₆ | Atmospheric pressure | 80 | 1.5 |
| Comparative conditions | C | 10% K₂S₄O₆ | Atmospheric pressure | RT | 1.5 |
| Comparative conditions | D | Purified water 8 ppm O₂ | 8.3 | 288 | 1~3 |
| Comparative conditions | E | Actual reactor water 0.2 ppm O₂ | Saturated vapor pressure | 288 | High residual stress |

TARGET AREA FOR SCC INITIATION

SILICON RUBBER COATING APPLIED ON TEST PIECE AT AN AREA WHERE NO SCC INITIATION WAS INTENDED

TEST PIECE HOLDING WASHER

TEST PIECE WITH APPLIED BEND STRAIN

FIG. 7

| Test No. | Test solution designation | Surrounding water | Pressure (MPa) | Solution temperature (°C) | Load strain (%) | Testing time (hr) | Test results |
|---|---|---|---|---|---|---|---|
| 1 | A | 1% K$_2$S$_4$O$_6$ | Atmospheric pressure | RT | 1.5 | 72 | IGSCC |
| 2 | B | 1% K$_2$S$_4$O$_6$ | Atmospheric pressure | 80 | 1.5 | 120 | IGSCC+Pitting corrosion |
| 3 | C | 10% K$_2$S$_4$O$_6$ | Atmospheric pressure | RT | 1.5 | 72 | IGSCC+IGC |
| 4 | A | 1% K$_2$S$_4$O$_6$ | Atmospheric pressure | RT | 0 | 168 | No IGC |
| 5 | B | 1% K$_2$S$_4$O$_6$ | Atmospheric pressure | 80 | 0 | 264 | IGC |
| 6 | C | 10% K$_2$S$_4$O$_6$ | Atmospheric pressure | RT | 0 | 168 | IGC |
| 7 | D | Purified water 8 ppm O$_2$ | 8.3 | 288 | 1~3 | 1000~3000 | IGSCC |
| 8 | E | Actual reactor water 0.2 ppm O$_2$ | Saturated vapor pressure | 288 | High residual stress | >200000 | IGSCC |

TEST NO. 2: 1% K₂S₄O₆, 80°C

PITTING CORROSION WAS INITIATED ON THE SURFACE OF TEST PIECE WITHOUT PRONOUNCED LARGE CRACKS.

SILICONE RUBBER COATING HAS BEEN REMOVED.

TEST NO. 3: 10 % $K_2S_4O_6$, RT

SILICONE RUBBER COATING APPLIED ON TEST PIECE AT AN AREA WHERE NO SCC INITIATION WAS INTENDED.

IGSCC INITIATED

FIG. 11

TEST NO. 1:
1% K$_2$S$_4$O$_6$, RT
72-HOUR TEST

1mm

OBSERVATION RESULTS
OF CROSS-SECTION
WITH IGSCC INITIATED
IN ALLOY 182

OBSERVATION RESULTS OF FRACTURE SURFACE WITH IGSCC INITIATED IN ALLOY 182

0.3mm

TEST NO. 1:
1% K2S4O6, RT
72-HOUR TEST

FIG. 17

| Test No. | K₂S₄O₆ (%) | pH | Temp. (°C) | NaCl (%) | TP1 (mm) | TP2 (mm) | S/N Ratio (db) |
|---|---|---|---|---|---|---|---|
| 1 | 1 | 4.5 | 25 | 0 | 7.08 | 0.1 | -17.0 |
| 2 | 1 | 3 | 40 | 0.1 | 10 | 9.17 | 19.6 |
| 3 | 1 | 1 | 60 | 1 | 5 | 8 | 15.6 |
| 4 | 3 | 3.8 | 40 | 1 | 10 | 10 | 20.0 |
| 5 | 3 | 3 | 60 | 0 | 10 | 10 | 20.0 |
| 6 | 3 | 1 | 25 | 0.1 | 7.8 | 1.25 | 4.8 |
| 7 | 6 | 3.6 | 60 | 0.1 | 10 | 10 | 20.0 |
| 8 | 6 | 3 | 25 | 1 | 8.75 | 5.85 | 16.7 |
| 9 | 6 | 1 | 40 | 0 | 7.5 | 8.75 | 18.1 | pH: Adjusted with H₂SO₄ except for Tests Nos. 1, 4 and 7.

FIG. 18A

| $K_2S_4O_6$ (%) | S/N Ratio (db) |
|---|---|
| 1 | 6 |
| 3 | 15 |
| 6 | 18 |

FIG. 18B

| pH | S/N Ratio (db) |
|---|---|
| 6 | 7 |
| 4.5 | 8 |
| 3 | 19 |
| 1 | 13 |

FIG. 18C

| Temp. (°C) | S/N Ratio (db) |
|---|---|
| 25 | 2 |
| 40 | 19 |
| 60 | 19 |

FIG. 18D

| NaCl (%) | S/N Ratio (db) |
|---|---|
| 0 | 7 |
| 0.1 | 15 |
| 1 | 17 |
| 10 | 19 |

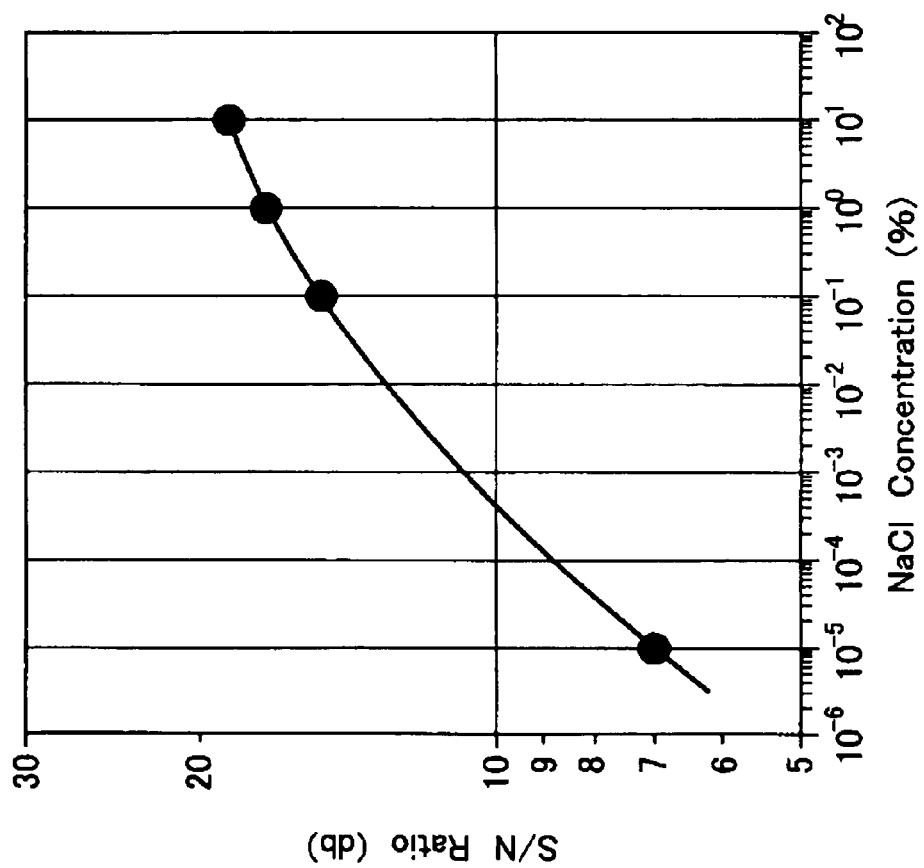

FIG. 23

| Test No. | Test solution designation | Surrounding water | Pressure (MPa) | Solution temperature (°C) | Specimen | Testing time (hr) | Test results |
|---|---|---|---|---|---|---|---|
| M1 | A (Invention) | 1% K$_2$S$_4$O$_6$ | Atmospheric pressure | RT | Welded specimen of Alloy 182/600 (Surface finishing: grinder) | 144 | IGSCC initiated |
| M2 | A (Invention) | 1% K$_2$S$_4$O$_6$ | Atmospheric pressure | RT | Welded specimen of Alloy 182/600 (Surface finishing: buffing) | 168 | IGSCC initiated |

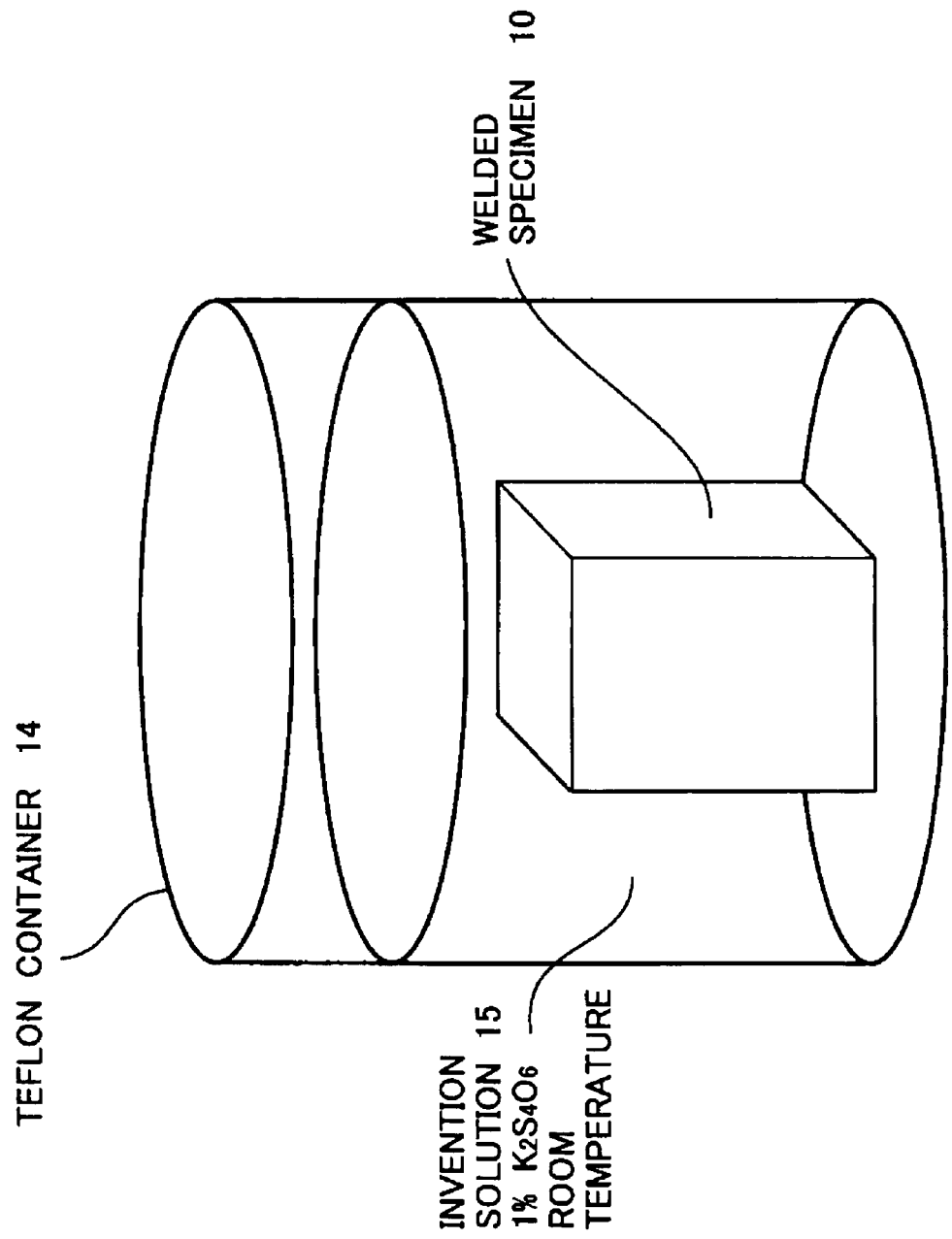

OBSERVATION RESULTS OF FRACTURE SURFACE WITH IGSCC INITIATED IN ALLOY 182

TEST NO. M2
168-HOUR TEST

FIG. 28
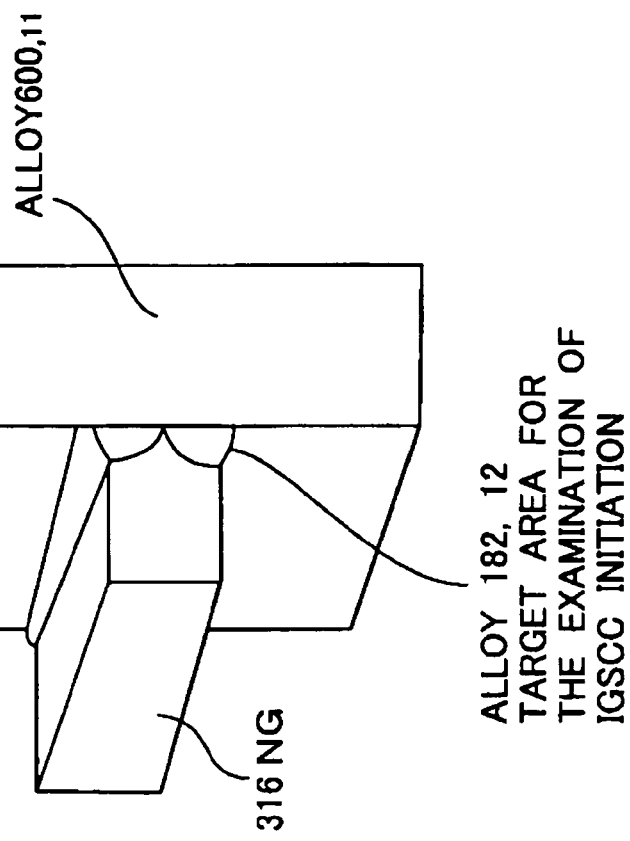
WELDED SPECIMEN ②
ALLOY600,11
ALLOY 182, 12
TARGET AREA FOR
THE EXAMINATION OF
IGSCC INITIATION
316 NG
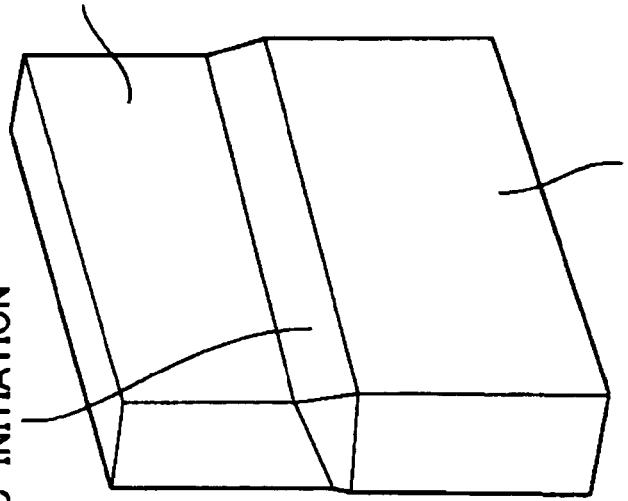
WELDED SPECIMEN ①
316 NG,16
ALLOY 182, 12
TARGET AREA FOR
THE EXAMINATION OF
IGSCC INITIATION
ALLOY600,11

FIG. 39

| C | Si | Mn | P | Ni | Cr | Vol.% of Ferrite |
|---|---|---|---|---|---|---|
| 0.049 | 0.36 | 1.39 | 0.014 | 9.9 | 19.03 | 8 |

FIG. 40

| Welding rod diameter (mm) | Current (A) | Voltage (V) | Welding speed (cm/min) | Heat input (kj/cm) | Interlayer temperature (°C) |
| --- | --- | --- | --- | --- | --- |
| 4 | 135 | 25 | 16 | 1.27 | 90~200 |

FIG. 42

| Conditions No. | Heat treatment temperature | Heat treatment time |
|---|---|---|
| 1 | 610°C | 6hr |
| 2 | 610°C | 10hr |
| 3 | 610°C | 20hr |
| 4 | 610°C | 30hr |
| 5 | 610°C | 40hr |

FIG. 43

| Test | Test solution | Test temperature | Testing time (hr) | Determination |
|---|---|---|---|---|
| ASTM A262E | 16% H$_2$SO$_4$ +6.4% CuSO$_4$ +Cu | Boiling temperature | 24hr | Visual observation of bent test piece |
| Modified ASTM A262E | 16% H$_2$SO$_4$ +6.4% CuSO$_4$ +Cu | Boiling temperature | 24hr | Depth of IGC in a cross-section of bent test piece |

308SS, 610°C/6hr

METHOD OF CAUSING INTERGRANULAR STRESS CORROSION CRACK TO GENERATE AND GROW IN SAMPLE

TECHNICAL FIELD

This invention relates to a maintenance technique for intergranular stress corrosion cracking (hereinafter abbreviated as "IGSCC") known as environmentally-assisted cracking in a weld of a structure, for example, in a nuclear power plant, and especially to a technique which can cause IGSCC to initiate and grow by a simple and easy method in a specimen capable of retaining corrosion resistance through passivation.

BACKGROUND ART

Under the current circumstances, the construction of new nuclear power plants is difficult although there is an increasing worldwide requirement for successfully dealing with both a reduction in $CO_2$ emission and an increase in electricity demand. For the extension of the operational life of each existing nuclear power plant operated over along period, it is therefore important to determine the soundness of materials of its equipment and the like such as its reactor and in-core structures and weld zones therein.

As a method for non-destructively detecting and determining the existence or non-existence of cracks formed through IGSCC in the materials of equipment such as a reactor due to conditions such as quality, stress and use environment as well as their dimensions, shapes and the like in the actual equipment, it can be contemplated to apply ultrasonic examination technology, eddy current examination technology or the like.

For the extensive application of the detection and determination of cracks by the above-described technology to positions exposed to various conditions, however, it is necessary to repeat the detection and determination of cracks by using specimens with IGSCC, which occur under various conditions in actual equipment, reproduced experimentally therein and to accumulate data.

Under conditions where a corrosion flaw other than IGSCC to be determined exists in combination, it is difficult to accurately detect and determine a crack formed by IGSCC. There is, accordingly, an outstanding demand for the development of a technique that can experimentally cause only IGSCC to initiate and grow in a short time exclusively at an intended specific area although in actual equipment, IGSCC occurs after an extremely long time under conditions of high-temperature and high-pressure water.

FIGS. 2A and 2B are construction diagrams of a shroud support, which is one of the in-core structures in a pressure vessel in a nuclear power plant, and FIG. 2B is an enlarged view of a section X in FIG. 2A. These figures show the pressure vessel at numeral 100, legs 101 each arranged upright on a bottom part of the pressure vessel 100 via a weld 102, and a support cylinder 103 supported on the legs 101. The support cylinder is connected to each leg 101 via a weld 104. Designated at numeral 105 are support plates arranged between the pressure vessel 100 and the support cylinder 103 and connected to the pressure vessel 100 and the support cylinder 103 via welds 106.

Widely employed as the material of this structure is a nickel-based alloy or stainless steel which can retain corrosion resistance through passivation. With such a material, the application of stress to a sensitized area in the vicinity of grain boundaries (i.e., Cr-depleted area as a result of the deposition of chromium carbides) results in the initiation of a crack, followed by its growth. This is called "IGSCC".

As a method for causing IGSCC to initiate and grow in a partial specimen of a welded structure in equipment, said welded structure being capable of retaining corrosion resistance through passivation, an accelerated test has been widely used to date. This accelerated test is conducted using as a starting point a simulated defect, which has been formed artificially by cutting or electrical discharge machining, as is or a defect of weld crack, and takes a long time in high-temperature and high-pressure water.

Although not studied for the above purpose, there is ASTM G35 test [Wachenroder's solution, pH<1], which makes use of polythionic acid and may be used as a reference for the simple and easy initiation and growth of IGSCC. This method is known in connection with studies on IGSCC of sensitized stainless steel in desulfurization equipment in the petroleum refinery industry [see Matsushima et al: Boshoku Gijutsu (Corrosion Preventive Technology), 22(4), (1974)].

However, the above-mentioned test simulates the environment of desulfurization equipment. It has, therefore, been reported that the preparation of the test solution is not simple and easy and also that not only IGSCC but also an intergranular corrosion (IGC) attack occurs (see the non-patent publication referred to in the above). Therefore, cracking occurred under test conditions, under which IGC was observed, is considered to be a stress-accelerated IGC phenomenon rather than IGSCC.

As is appreciated from the foregoing, no simple and easy technique has heretofore been established for the development of only IGSCC without IGC or pitting corrosion at room temperature in the atmosphere except for the method that can cause IGSCC to initiate and grow by relying upon a long-time accelerated test in high-temperature and high-pressure water.

An object of the present invention is, therefore, to overcome the above-described drawbacks of the conventional techniques, and to provide a method for simply and easily causing only IGSCC to initiate and grow in a specimen, which can retain corrosion resistance through passivation, in a short time in the atmosphere.

DISCLOSURE OF THE INVENTION

To achieve the above-described object, a first aspect of the present invention is characterized by bringing a specimen, which is made of a material capable of retaining corrosion resistance through passivation, into contact with a solution of a tetrathionate salt such that intergranular stress corrosion cracking initiates and grows in the specimen.

A second aspect of the present invention is characterized in that the specimen is a welded structure or a simulated specimen of the welded structure, or a cut-out specimen cut out from the welded structure or the simulated specimen.

A third aspect of the present invention is characterized by providing means for applying a strain to the specimen such that the specimen is brought into contact with the tetrathionate salt solution while being applied with a strain by the means.

A fourth aspect of the present invention is characterized in that the means for applying a strain to the specimen is a weld applied to the specimen.

A fifth aspect of the present invention is characterized in that the means for applying a strain to the specimen is a member or device for applying a strain to the specimen from an outside.

A sixth aspect of the present invention is characterized in that the solution of the tetrathionate salt is an aqueous solution of potassium tetrathionate or sodium tetrathionate, and a concentrate of potassium tetrathionate or sodium tetrathionate, a temperature of the solution and a pH value of the solution are controlled to a range of from 0.3 to 6 wt. %, a range of from 5 to 60° C. and a range of from 3 to 6, respectively.

A seventh aspect of the present invention is characterized in that the aqueous solution of potassium tetrathionate or sodium tetrathionate contains chlorine in a range of from 0.06 to 6 wt. %, for example, by addition of NaCl or KCl.

An eighth aspect of the present invention is characterized in a concentration of the chlorine is controlled to a range of from 0.6 to 6 wt. %.

A ninth aspect of the present invention is characterized by covering the specimen with a non-metallic material at an area other than an area where initiation of the intergranular stress corrosion cracking is intended.

A tenth aspect of the present invention is characterized in that the non-metallic material is a silicone rubber or fluororubber.

An eleventh aspect of the present invention is characterized in that the specimen has a weld, and the weld is composed of a nickel-base alloy or stainless steel.

A twelfth aspect of the present invention is characterized in that the specimen contains C, Nb and Ti, and a stabilization parameter of a material making up the specimen as determined by the following formula is 12 or smaller:

Stabilization parameter=0.13×[(Nb+2Ti)/C]

where C, Nb and Ti represent contents of the respective constituent materials as expressed in terms of wt. %.

A thirteenth aspect of the present invention is characterized by applying heat treatment to the specimen to bring the specimen into a sensitized state before causing the intergranular stress corrosion cracking to initiate in the specimen.

A fourteenth aspect of the present invention is characterized in that the heat treatment is applied to the specimen within the following temperature range:

500° C.≦T ° C.≦650° C.

and the following time range:

$t_1$ hours≦t hours≦$t_2$ hours where $$t_1 = 6 \exp\left\{\frac{Q}{R}\left(\frac{1}{T+273} - \frac{1}{883}\right)\right\}$$

$$t_2 = 15 \exp\left\{\frac{Q}{R}\left(\frac{1}{T+273} - \frac{1}{883}\right)\right\}$$

Q=50,000 to 60,00 cal/mol, and
R=1.987 calK$^{-1}$mol$^{-1}$.

A fifteenth aspect of the present invention is characterized in that the specimen has a weld, and the weld is composed of a ferrite-containing austenite stainless steel.

A sixteenth aspect of the present invention is characterized in that the specimen has a weld, a surface of a weld bead of the weld is ground at an area thereof where initiation of intergranular stress corrosion cracking is intended, and the solution of the tetrathionate salt is brought into contact with the thus-ground surface.

A seventeenth aspect of the present invention is characterized in that a dam is formed on the specimen in a vicinity of an area where initiation of intergranular stress corrosion cracking is intended, and the solution of the tetrathionate salt is poured into the dam to cause the intergranular stress corrosion cracking to initiate and grow in or around the weld.

An eighteenth aspect of the present invention is characterized in that the specimen is a welded structure in a nuclear power plant or a simulated specimen of the welded structure, or a cut-out specimen cut out from the welded structure or the simulated specimen.

BRIEF DESCRIPTION OF THE DRAWINGS

FIG. 3 is a table showing illustrative chemical compositions of nickel-based alloy test pieces for use in embodiments of the present invention.

FIG. 4 is a table showing test conditions for the initiation and growth of IGSCC.

FIG. 7 is a table showing test conditions for the initiation and growth of IGSCC and the test results.

FIG. 11 shows photographs of the conditions of cracking of a test piece to which a stress strain had been applied.

FIG. 17 is a table showing test conditions for the initiation and growth of IGSCC and the test results.

FIGS. 18A through 18D are tables showing test conditions for the initiation and growth of IGSCC versus SN ratios.

FIG. 19 is a graphic diagram of the addition of NaCl versus SN ratio.

FIG. 23 is a table showing two kinds of test conditions and the test results.

FIG. 24 is a view depicting an illustrative test arrangement.

FIG. 28 shows perspective views of further specimens.

FIG. 39 is a table showing an illustrative chemical composition of an austenite stainless steel weld metal.

FIG. 40 is a table showing welding conditions upon preparing a specimen.

FIG. 42 is a table showing the conditions of heat treatment for the specimen.

FIG. 43 is a table showing the test conditions of the modified ASTM A262E method.

BEST MODES FOR CARRYING OUT THE INVENTION

With reference to the drawings, a description will next be made in detail about a method according to an embodiment of the present invention for the initiation and growth of IGSCC in a specimen.

Figure 1:
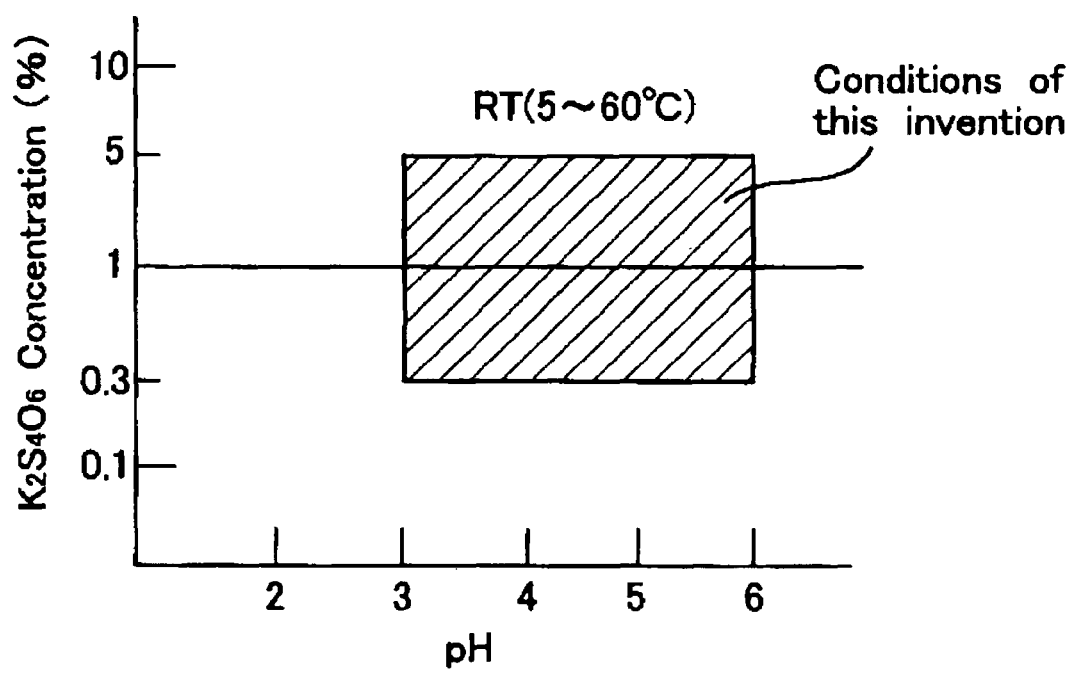
FIG. 1 is a graphic diagram showing a range of test conditions of this invention.
Figure 2A:
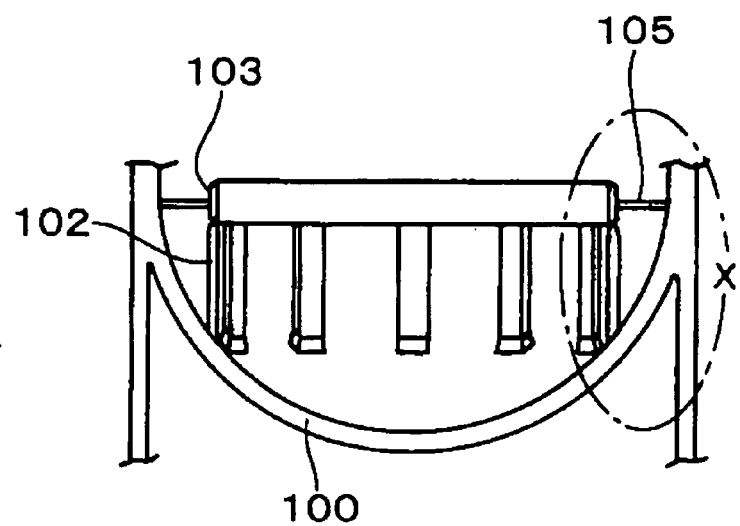
FIGS. 2A and 2B are views illustrating an in-core structure of a pressure vessel in a nuclear power plant.
Figure 2B:
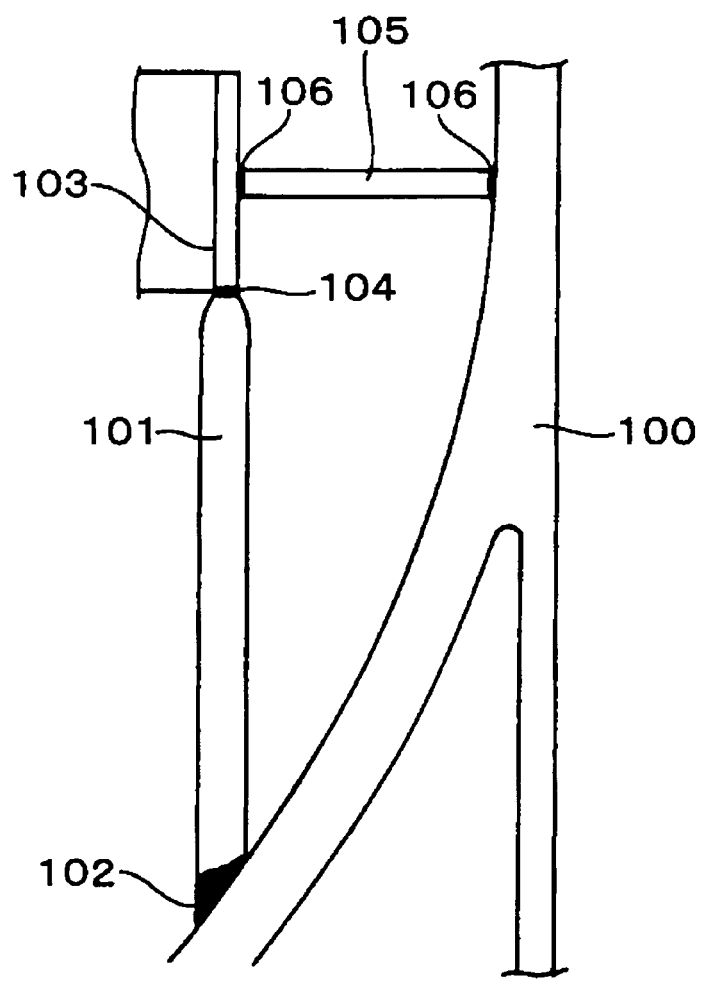

FIG. 1 is a graphic diagram showing conditions for a test solution in the present invention. As indicated by hatching in the figure, an aqueous solution of potassium tetrathionate ($K_2S_4O_6$) or sodium tetrathionate ($Na_2S_4O_6$) having a concentration of from 0.3 to 6 wt. % and a pH value of from 3 to 6 (hereinafter to be mentioned about the aqueous solution of potassium tetrathionate as a representative example) is brought into contact with a specimen at a temperature of from 5 to 60° C. under the present invention.

The specimen may be brought into contact with the aqueous solution of potassium tetrathionate under the above-described conditions while being covered, as needed, with a non-metallic material such as a silicone rubber of fluororubber at a metal surface other than an area where IGSCC is intended to grow in the test piece.

If needed to sensitize the specimen, the stabilization parameter of the material of at least a portion of the specimen can be controlled to 12 or lower, or stress relief annealing can be applied to the test piece at around 600° C., followed by application of low-temperature aging at 288 to 550° C.

The stabilization parameter is determined by the following formula:

Stabilization parameter=0.13×[(Nb+2Ti)/C]

where C, Nb and Ti indicate the contents of the respective constituent materials as expressed in terms of wt. %.

FIG. 3 is a table showing the chemical compositions of Alloy 182 and Alloy 600 as examples of a nickel-base alloy usable as a specimen in the present invention. As shown in the table, Alloy 182 and Alloy 600 both have a Ni content higher than 70 wt. %.

The stabilization parameter of Alloy 182 is 7.3 or smaller, while that of Alloy 600 is 1.5 or smaller. As their stabilization parameters are both smaller than 12, specimens can be sensitized by stress relief annealing at 600° C. and low-temperature aging at 288 to 550° C.

FIG. 4 shows the conditions (test solution designations: A to D) for tests conducted to establish a technique for the initiation and growth of IGSCC, and also, the conditions (test solution designation: E) for an IGSCC test in high-temperature water as estimated from technical papers. Under the invention conditions A shown in the table, the test is conducted at atmospheric pressure and room temperature (RT) with a 1 wt. % aqueous solution of (pH value: about 5) without adding any acid for pH adjustment.

On the other hand, the comparative conditions B are different from the invention conditions A in that the temperature has been raised to 80° C. The comparative conditions C are different from the invention conditions A in that the concentration of the aqueous solution of $K_2S_4O_6$ has been raised to 10%. The comparative conditions D are the conditions for a crevice SCC test at a pressure of 8.3 MPa in high-temperature water (solution temperature: 288° C.). The comparative conditions E are SCC conditions simulating the environment in actual equipment, the surrounding water is actual reactor water with 0.2 ppm of dissolved oxygen contained therein, and the pressure and solution temperature were the saturated vapor pressure and 288° C., respectively.

Figure 5:
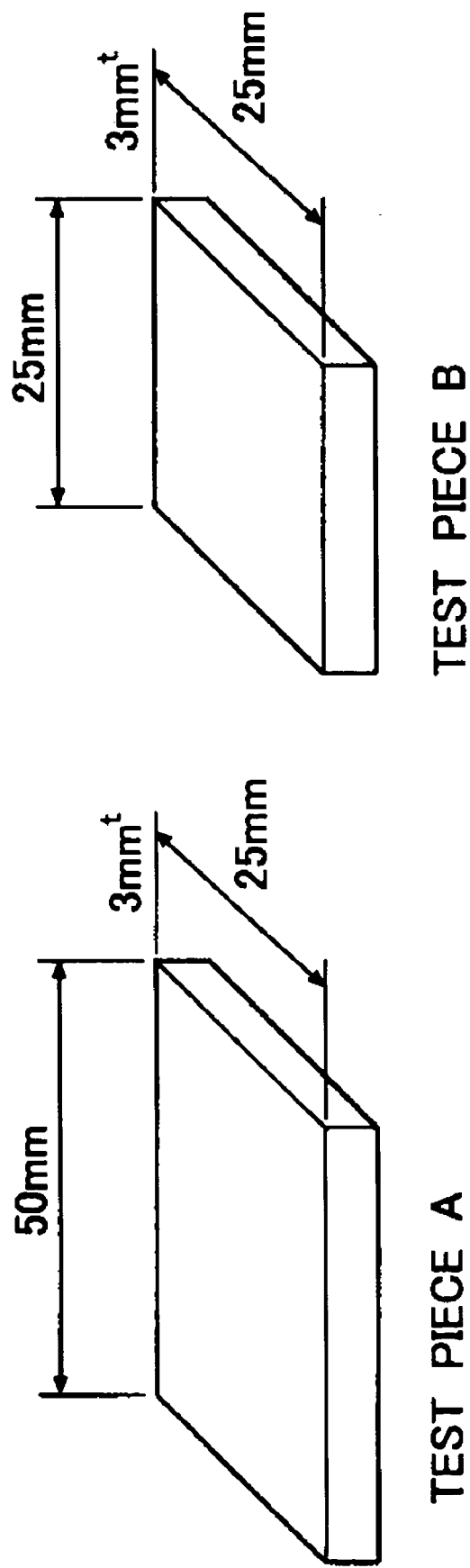
FIG. 5 shows perspective views of test pieces for use in embodiments of the present invention.

FIG. 5 shows perspective views of test pieces for use in tests under the invention condition A, the comparative conditions B and the comparative conditions C. The test piece A is a test piece of Alloy 182 weld metal for IGSCC-initiating, fixed-strain bend test. The test piece B is a test piece of sensitized Alloy 600 for investigating whether or not IGC or pitting corrosion has occurred or not.

Figure 6A:
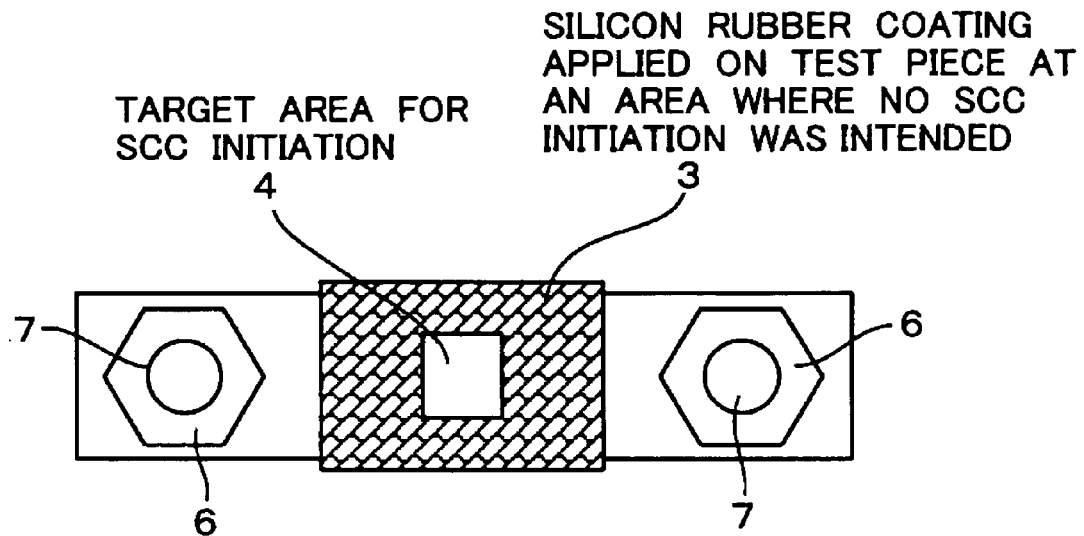
FIGS. 6A and 6B are views illustrating one of the test pieces in a state mounted on a jig.
Figure 6B:
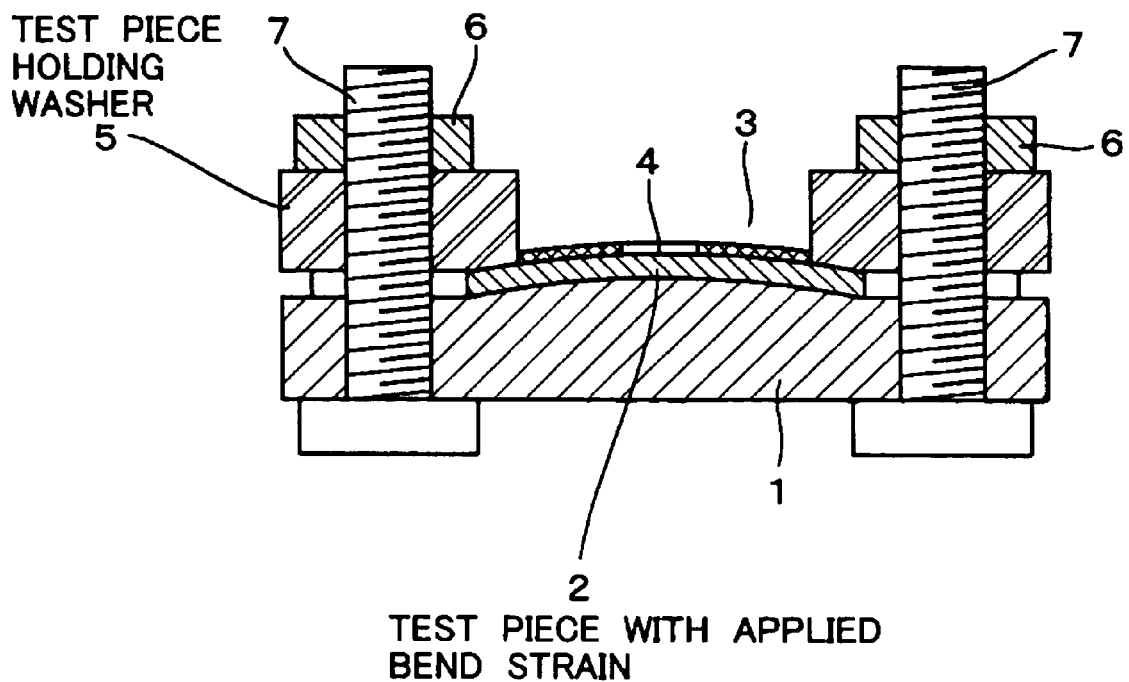

In FIGS. 6A and 6B, the test piece A for fixed-strain bend test is mounted on a jig by bolts and nuts to develop a load (bend) strain to 1.5%. The figures depict the bend-strain applying jig 1 with an upper surface thereof bulging out in a slightly curved profile, the test piece 2 set on the jig 1 under the bend strain applied thereto, a silicone rubber coating 3 covering the test piece 2 at an area other than a central area such that the area where initiation of IGSCC is intended can be limited, a target IGSCC initiation area 4 over which the coating 3 is not applied, test piece holding washers 5, bolts 6, and nuts 7. By setting the test piece 2 on the jig 1 as illustrated in FIG. 4, a fixed bend strain is loaded on the test piece 2 from the outside.

FIG. 7 is a table in which the results of those tests are summarized, and presents the test conditions (surrounding water, pressures, solution temperatures, load strains), testing time, and the results of examinations as to whether or not the cracking was IGSCC. In the table, Tests Nos. 1 to 6 were each studied as an alternative testing method of the test in high-temperature and high-pressure water of 288° C., said test requiring a long time to initiate IGSCC as demonstrated in Tests Nos. 7 and 8. It is to be note that the value of the testing time in Test No. 8 was a value estimated from empirical data.

Figure 8:
FIG. 8 is a photograph showing the conditions of a test piece, to which a stress strain had been applied, after the test piece was tested.

FIG. 8 shows a surface of the test piece after tested for 72 hours in Test No. 1 (1 wt. % aqueous solution of $K_2S_4O_6$, atmospheric pressure, solution temperature: room temperature, load strain: 1.5%) shown in FIG. 7. According to examinations conducted in the course of the test, it was confirmed that microcracks (fine cracks) occurred at the $24^{th}$ hour and cracks were visually observed at the $48^{th}$ hour. Indicated by an arrow in FIG. 8 is a silicone rubber coating applied to the test piece at an area where initiation of SCC was not intended. Initiation of IGSCC is observed at a central area in the figure.

Figure 9:
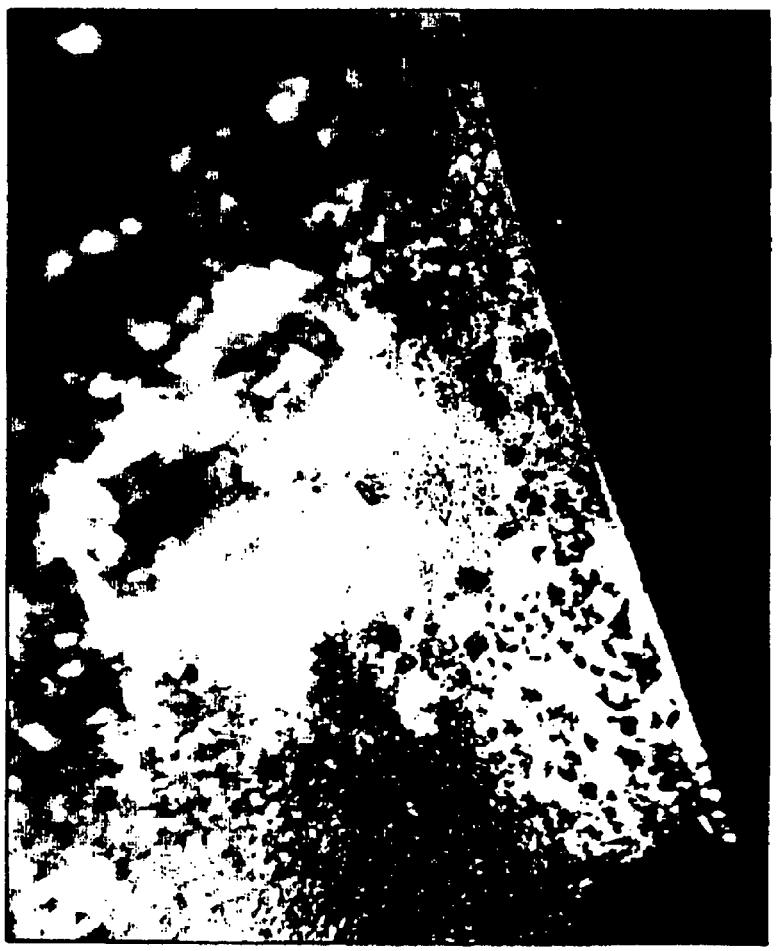
FIG. 9 is a photograph showing the conditions of cracking of a test piece to which a stress strain had been applied.

FIG. 9 shows a surface of the test piece after tested for 120 hours in Test No. 2 (1 wt. % aqueous solution of $K_2S_4O_6$, atmospheric pressure, solution temperature: 80° C., load strain: 1.5%) shown in FIG. 7. IGSCC was hard to initiate, and pitting corrosion was observed. As IGSCC as hard to initiate, the testing time took as much as 120 hours. According to the photograph, pitting corrosion initiated on the surface of the test piece without any pronounced large cracks. The photograph was taken after removing the silicone rubber coating.

Figure 10:
FIG. 10 is a photograph showing the conditions of a test piece, to which a stress strain had been applied, after the test piece was tested.

FIG. 10 shows a surface of the test piece after tested for 72 hours in Test No. 3 (10 wt. % aqueous solution of $K_2S_4O_6$, atmospheric pressure, solution temperature: room temperature, load strain: 1.5%) shown in FIG. 7. It was confirmed in the course of the test that microcracks (fine cracks) occurred at the $24^{th}$ hour and cracks (IGSCC+IGC) were visually observed at the $48^{th}$ hour in a central part of the photograph. Therefore, the cracking in each of Tests Nos. 2 and 3 was not true IGSCC but was a stress-accelerated IGC phenomenon.

Figure 12:
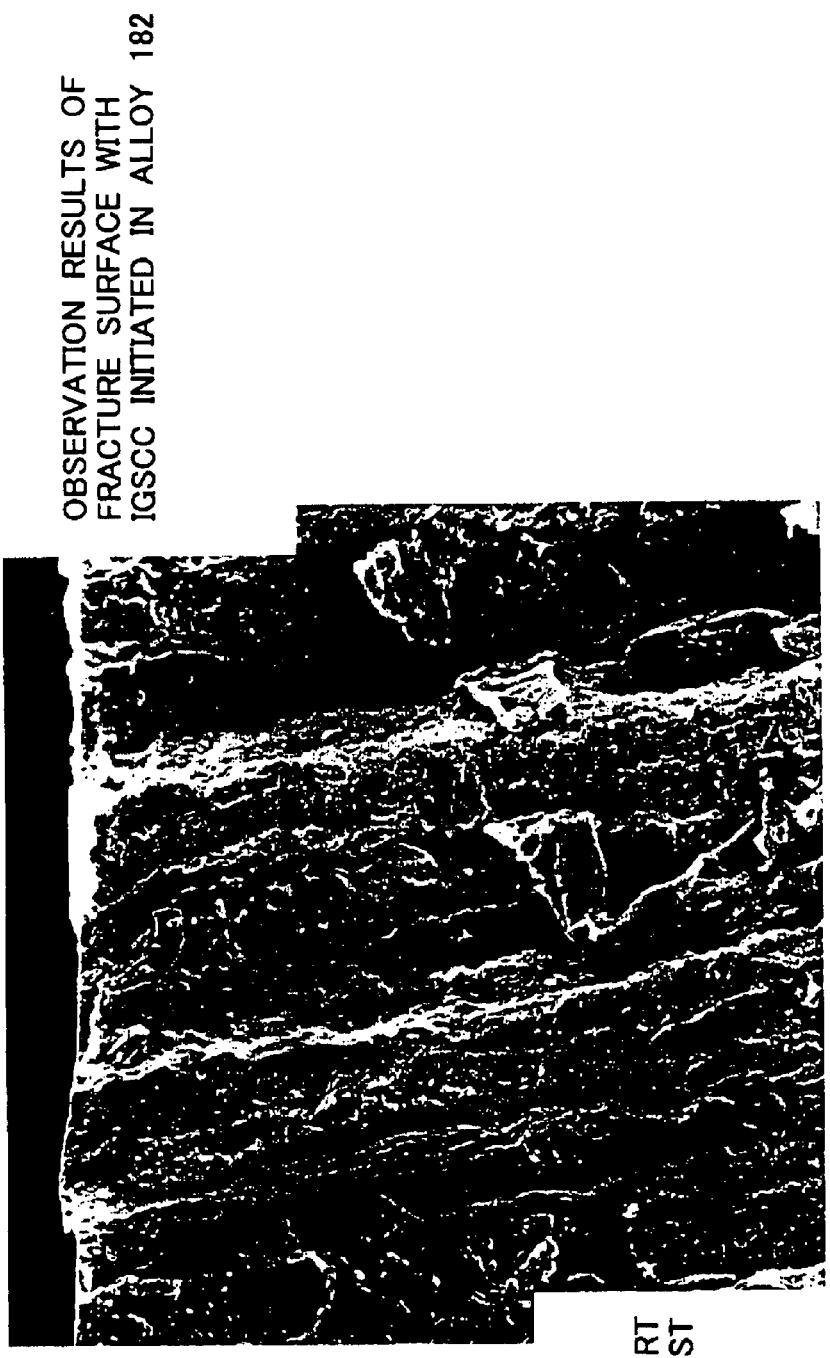
FIG. 12 is a photograph showing the conditions of cracking of a test piece to which a stress strain had been applied.

FIG. 11 shows photographs of the conditions of cracking occurred in Alloy 182 as a result of Test No. 1 as viewed in a cross-section, and FIG. 12 is an enlarged photograph showing the details of a fracture surface of the alloy. As shown in these photographs, the cracking occurred along grain boundaries, and this cracking was confirmed to be IGSCC.

Figure 13:
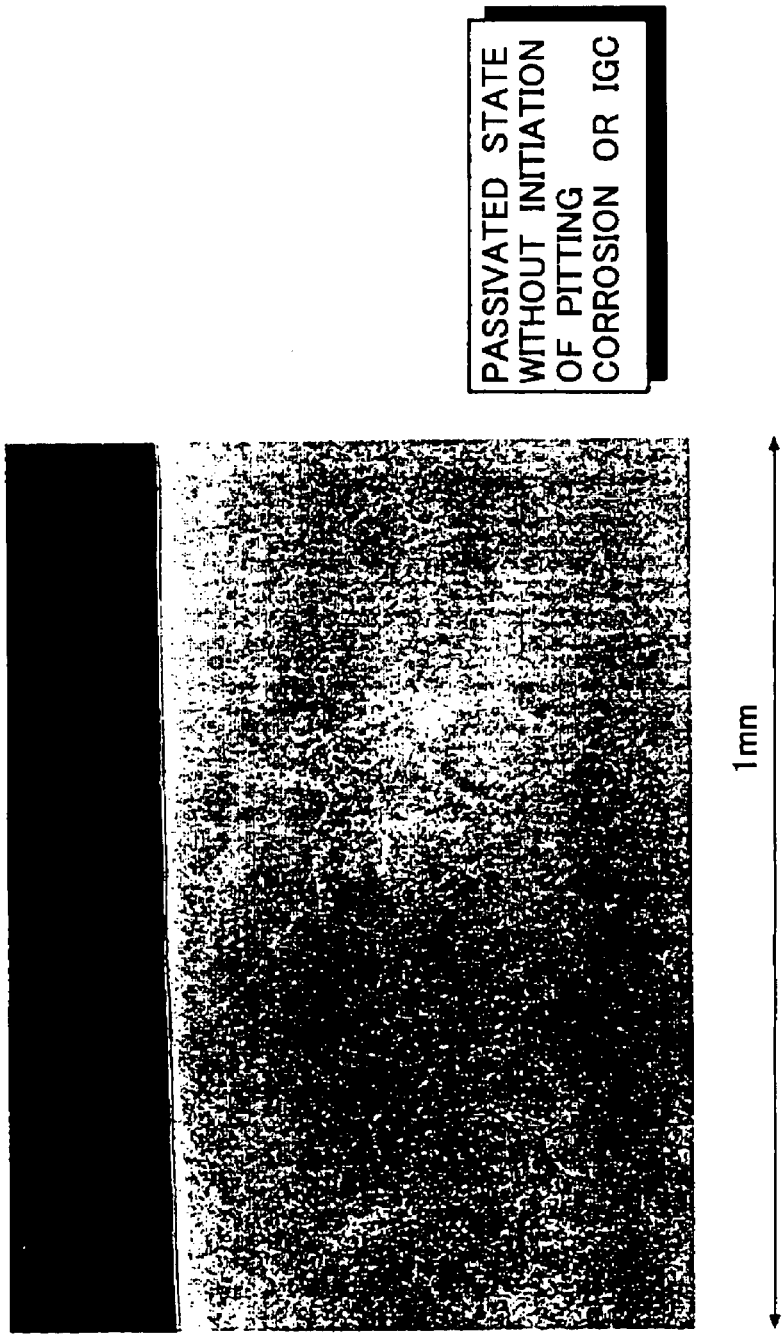
FIG. 13 is a photograph showing the conditions of a test piece, to which a stress strain had not been applied, after the test piece was tested.

FIG. 13 shows a cross-section of the test piece in a slightly bent form after conducting Test No. 4 (1 wt. % aqueous solution of $K_2S_4O_6$, atmospheric pressure, solution temperature: room temperature, load strain: 0%, testing time: 168 hours) in which the immersion of the long time was conducted without applying any fixed-strain bend. As shown in the photograph, the test piece was in a passivated state without observation of any pitting corrosion or IGC.

Figure 14:
FIG. 14 is a photograph showing the conditions of a test piece, to which a stress strain had not been applied, after the test piece was tested.

FIG. 14 shows a cross-section of the test piece in a slightly bent form after conducting Test No. 5 (1 wt. % aqueous solution of $K_2O_{406}$, atmospheric pressure, solution temperature: 80° C., load strain: 0%, testing time: 264 hours) in which the immersion of the long time was conducted without applying any fixed-strain bend. As shown in the photograph, pitting corrosion and IGC were observed.

Figure 15:
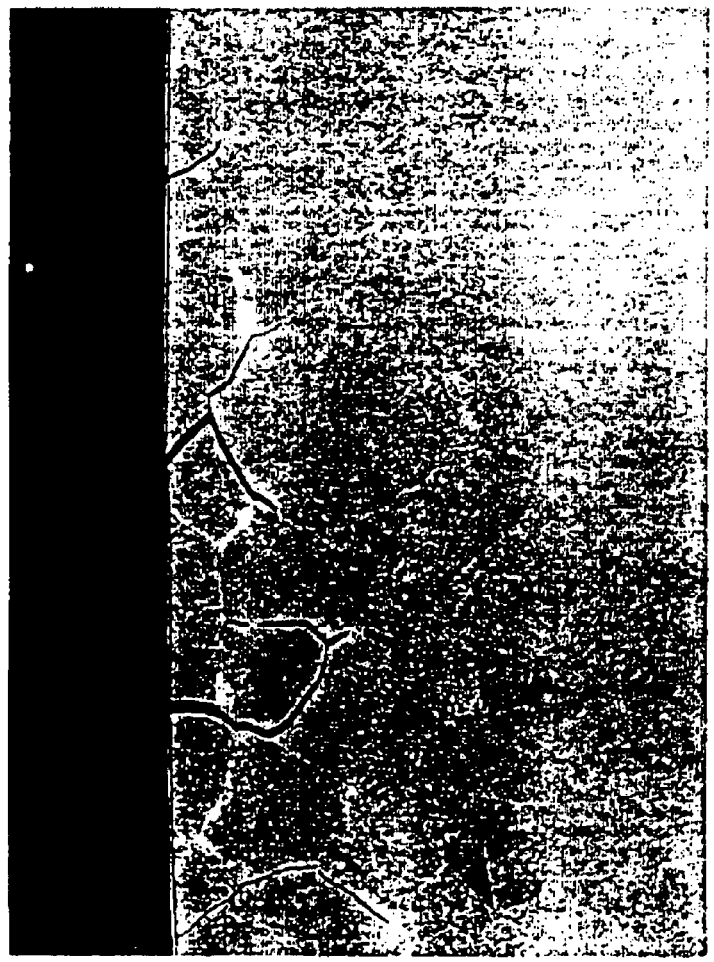
FIG. 15 is a photograph showing the conditions of a test piece, to which a stress strain had not been applied, after the test piece was tested.

FIG. 15 shows a cross-section of the test piece in a slightly bent form after conducting Test No. 6 (10 wt. % aqueous solution of $K_2S_4O_6$, atmospheric pressure, solution temperature: room temperature, load strain: 0%, testing time: 168 hours) in which the immersion of the long time was conducted without applying any fixed-strain bend. As shown in the photograph, IGC was observed.

It has been confirmed from these test results that IGC occurs when the temperature of a solution is raised to 80° C. or the concentration of an aqueous solution of $K_2S_4O_6$ is raised to 10%.

In FIG. 7, Test No. 7 and Test No. 8 show the conditions of tests by conventional methods for the initiation and growth of IGSCC and the results of the tests. For the initiation and growth of IGSCC, Test No. 7 required as much as from 1,000 to 3,000 hours, and Test No. 8 is considered to require an extremely long time in excess of 200,000 hours based on a value estimated from laboratory data.

Figure 16:
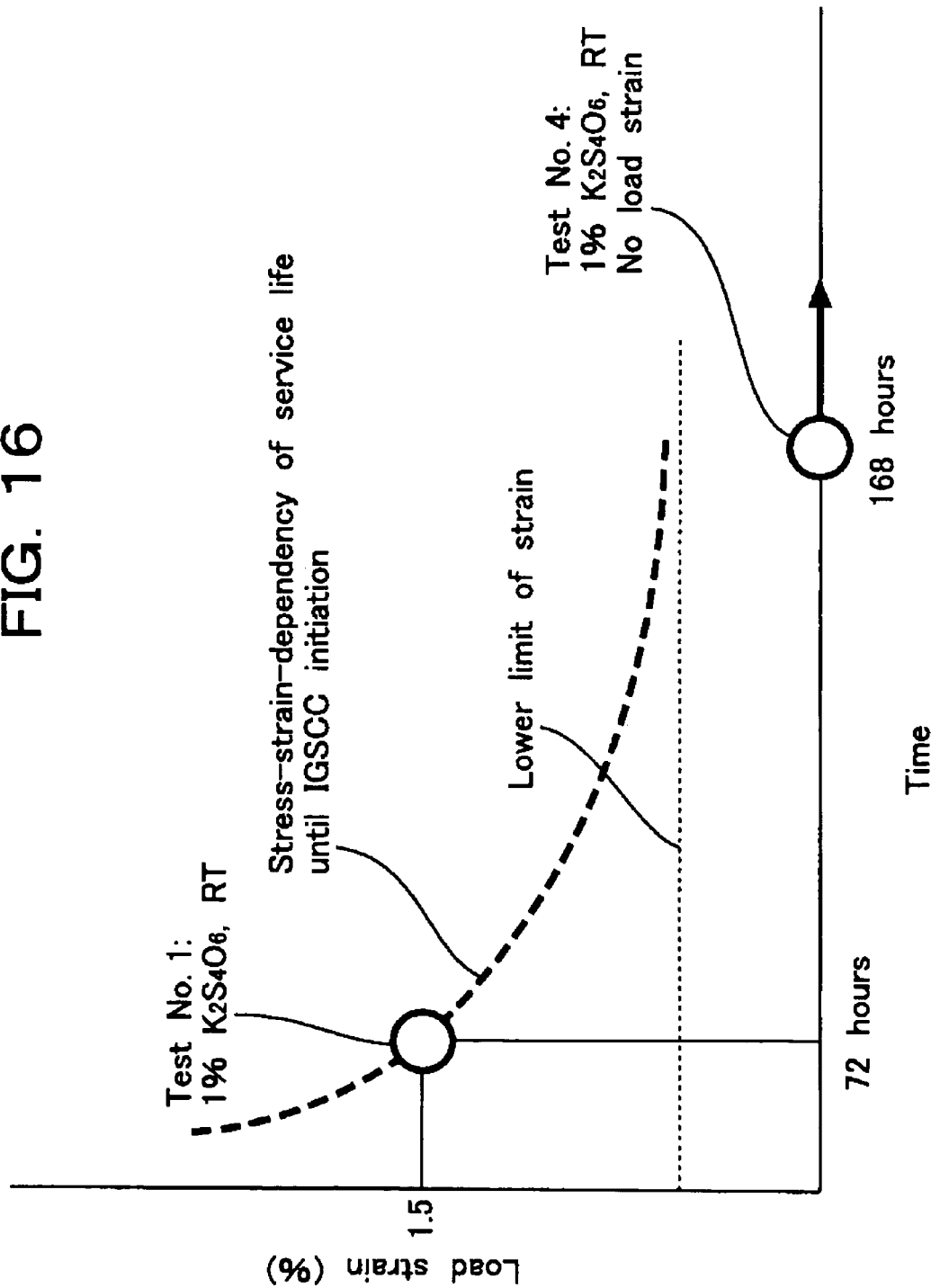
FIG. 16 is a conception diagram of effects of a load strain on the service life until SCC initiation.

Under the solution conditions A of Tests Nos. 1 and 4, said solution conditions A meeting the conditions of the present invention, no cracking occurs unless a stress strain is applied but cracking takes place when a stress strain is applied. Therefore, as illustrated in FIG. 16, the initiation and growth time of IGSCC are considered to have strain-dependency, and are also considered to be explainable based on the film-destructive cracking mechanism [in this respect, reference may be had to Pugh: Environment-Sensitive Mechanical Behavior, page 351, Cordenand Breach, N.Y., (1966)].

Moreover, the cracking is of the IGSCC type because it grew by selecting only grain boundaries. This is equivalent to IGSCC of a sensitized nickel-based alloy in oxygen-containing water obtained in Test No. 7 or Test No. 8 in FIG. 7. However, the composition and properties of a film are considered to differ depending on the conditions for its formation.

From the results of the above study, the test conditions of the present invention were limited to the hatched area shown in FIG. 1. The lower limit of the concentration of the aqueous solution of $K_2S_4O_6$ has been set at 0.3 wt. % in the conditions of the present invention because, as IGSCC occurs in 24 hours even at 1 wt. %, it is desired to make it possible to use the method of the present invention even when a need arises to delay the initiation time of IGSCC in the case of a high-stress welded structure. The setting of the upper limit of the concentration at 6 wt. % is attributed to the possibility of IGC initiation if the concentration is set at a level as high as 10 wt. %. The concentration of $K_2S_4O_6$ can, therefore, be in a range of from 0.3 to 6 wt. %, preferably from 0.5 to 3 wt. %.

The setting of the lower limit of the solution temperature at 5° C. is to avoid freezing of test solutions. The setting of the upper limit of the solution temperature at 60° C. is to inhibit the occurrence of pitting corrosion or IGC. Accordingly, the solution temperature can be in a range of from 5 to 60° C., preferably from 10 to 30° C.

A metal area other than an area where the growth of IGSCC is intended can be covered with a non-metallic material such as a silicone rubber or fluororubber as needed. When covered as described above, IGSCC can be caused to initiate only at the partially exposed metal area by bringing a test solution into contact with the partially exposed metal area even in the case of a large welded equipment structure.

Further, the initiation of IGSCC can be facilitated by forming at least a portion of a welded structure with a material the stabilization parameter of which is 12 or smaller, or by applying heat treatment to a partial specimen of a welded structure 600° C. and then low-temperature aging to it at 288 to 550° C. such that the specimen is brought into a sensitized state.

A description will next be made about a method according to another embodiment of the present invention for the initiation and growth of intergranular stress corrosion cracking in a specimen. In this embodiment, the selection of test conditions was conducted in further detail by using an orthogonal table $L_9(3^4)$ in quality engineering.

The orthogonal table $L_9(3^4)$ is a sort of experimental design, which makes use of an orthogonal table. The "9" in $L_9$ represents the number of rows in the orthogonal table (this number corresponding to the number N of experiments upon allocation), the "3" in $3^4$ indicates that the numbers which make up each column each consists of three numerals (corresponds to the 3 levels of each factor), and the "4" of $3^4$ indicates that the number of columns is 4 columns (corresponds to the number of the factors).

FIG. 17 summarizes the results of a fixed-strain bend test conducted by allocating, as SCC-affecting factors, $K_2S_4O_6$ concentration, pH value, temperature and NaCl concentration in the orthogonal table $L_9$.

The $K_2S_4O_6$ concentration was set at 1, 3 and 6 wt. %. The pH value was set at 1, 3 and unadjusted condition in order to investigate its degree of influence. In Tests Nos. 4 and 7 in each of which the pH value was not adjusted as a condition, the pH values fell below 4. This is considered to be attributable to the high $K_2S_4O_6$ concentrations. The test temperature was set at 25, 40 and 60° C. for detailed observation. The addition of NaCl was effected on a trial basis to investigate any possible effect for shortening the time of an SCC test, and the content of NaCl was set at non-addition, 0.1 wt. % and 1 wt. %.

In the fixed-strain bend test, two test pieces were used for each test condition, and a 24-hour immersion test was conducted. To compare the readiness of cracking in the respective tests, the test results were summarized as shown in FIG. 17. Specifically, the total length and number of surface cracks of IGSCC occurred in the surface of each test piece were determined, and the crack length per crack was then determined. Using the results, the SN ratio of large characteristics was determined in accordance with the following formula, and the results are presented in FIG. 17.

$$SN = -10 \log \left\{ \frac{1}{n} \sum_{i=1}^{n} \left( \frac{1}{y_i} \right)^2 \right\}$$

where n stands for the number of data and $y_i$ is a characteristic value.

FIGS. 18A to 18D show factorial effects based on the SN ratios. FIG. 18A is a table showing variations in SN ratio depending on the $K_2S_4O_6$ concentration, FIG. 18B is a table showing variations in SN ratio depending on the pH value, FIG. 18C is a table showing variations in SN ratio depending on the temperature, and FIG. 18D is a table showing variations in SN ratio depending on the NaCl concentration.

As apparent from these tables, the SN ratio is higher and cracking is easier when the $K_2S_4O_6$ concentration is 3 wt. % or 6 wt. % than 1 wt. %. Concerning the pH value, cracking is relatively easier at pH 3, but cracking becomes difficult when the pH value is excessively lowered to 1. At low pH values, test pieces and a fixed-strain bend test jig made of SUS 304 show appearances of uniform or general corrosion and become black. Slower cracking at lowered pH values may possibly be related to this phenomenon. With respect to the temperature, cracking is easier at 40° C. or 60° C. than at 25° C.

When NaCl is added to the concentration of 0.1 wt. %, IGSSC is accelerated than that by the same solution without addition of NaCl. This can be appreciated well if FIG. 18D is converted into a graphic diagram as shown in FIG. 19. Accordingly, the upper limit of the NaCl concentration is 10 wt. %. As the molecular weight of NaCl is 58.5 and the atomic weight of Cl is 35.5, the 10 wt. % concentration of NaCl can be converted in to Cl concentration as follows: 10×(35.5/58.5)=6, that is, 6 wt. %, while the 0.1 wt. % concentration of NaCl can be converted to 0.06 wt. % in terms of Cl concentration. In terms of Cl concentration, the NaCl concentration can therefore be in a range of from 0.06 to 6 wt. %, preferably in a range of from 0.6 (which is equivalent to 1 wt. % in terms of the NaCl concentration) to 6 wt. %. KCl and the like are also considered to accelerate SCC owing to the film-deteriorating effect of chlorine, a similar test was conducted with KCl. As a result, it has also been found that the NaCl concentration can be in a range of from 0.06 to 6 wt. %, preferably in a range of from 0.6 to 6 wt. % in terms of the Cl concentration.

Figure 49:
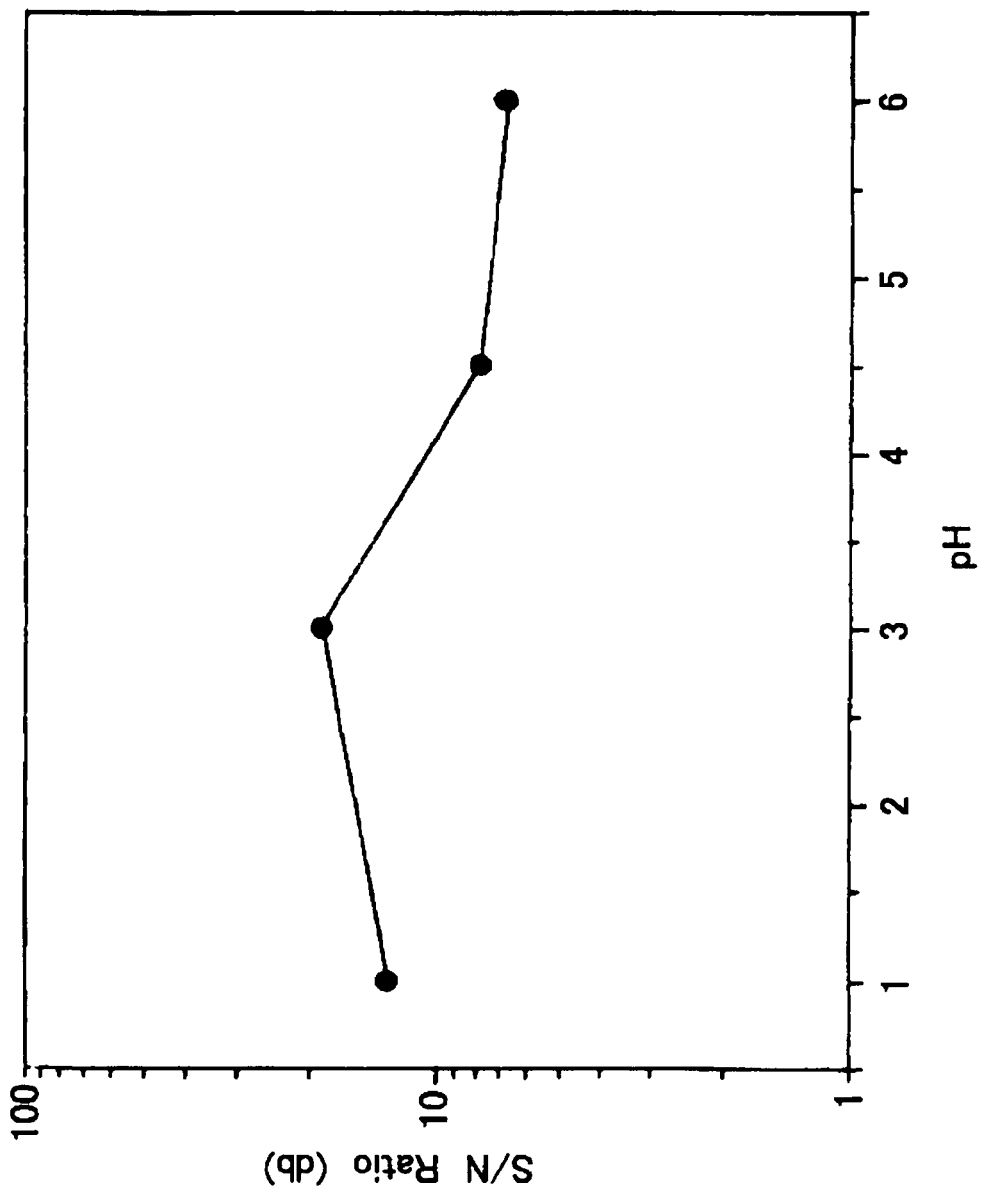
FIG. 49 is a graphic diagram of the pH value of test solution versus S/N.

Because a reduction in the pH value of the solution makes it possible to initiate not only IGSCC but also IGS, The lower limit of the pH value is set at 3. To raise the pH value, it is necessary to add another chemical in a large amount. This is inconvenient from the standpoint of handling so that the upper limit of the pH value is set at 6. As shown in FIG. 49, there is no substantial difference in S/N between the case of pH 4.5 and the case of pH 6, and the S/N at pH 4.5 is substantially equal to that at pH 6. Accordingly, the pH value of the solution can be from 3 to 6, preferably from 4.5 to 5.5.

From the results of the above study, the conditions suitable for the initiation of IGSCC in Alloy 182 were selectively determined as will be described hereinafter. When the concentration of $K_2S_4O_6$ is raised, the pH value is lowered to initiate IGC. The concentration of $K_2S_4O_6$ was, therefore, set at from 0.3 to 6 wt. %. The pH value was set at from 3 to 6 to avoid any initiation of IGC. The temperature was set at from 5 to 60° C. by also taking handling ease into consideration. The chlorine concentration was limited to a range of from 0.06 to 6 wt. % with a view to accelerating SCC.

Figure 20:
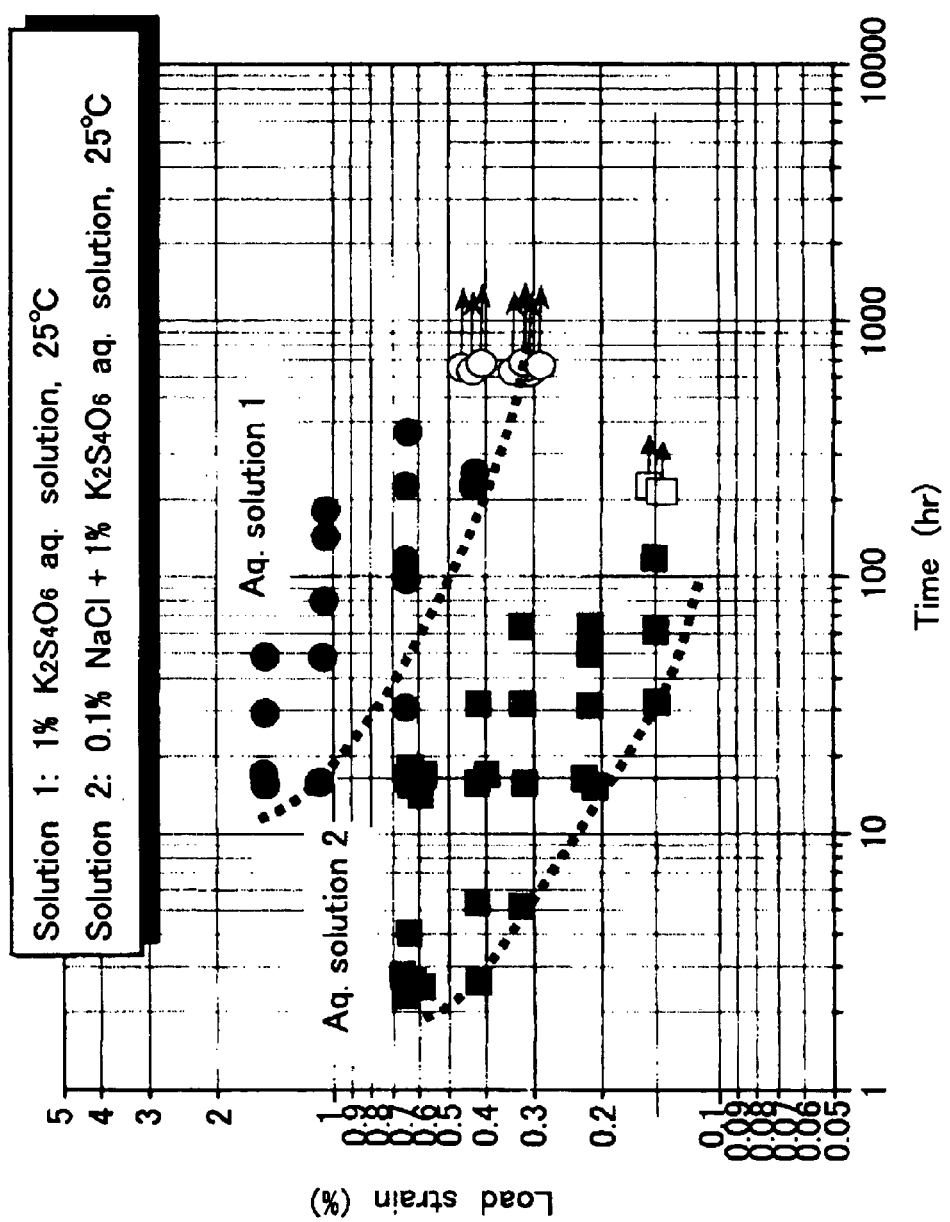
FIG. 20 is a graphic diagram showing effects of load strain on the service life of Alloy 180 until SCC in test solutions.

FIG. 20 illustrates the bend-strain-dependency of sensitized Alloy 182 in the solution 1 (an aqueous solution of 1% $K_2S_2O_6$) and the solution 2 (an aqueous solution of 0.1% NaCl+1% $K_2S_2O_6$) as determined by an OBB test. As apparent from the graphic diagram, the service life until the initiation of IGSCC in the solution 2 was as short as one hundredth of the service life until the initiation of IGSCC in the solution 1. It is, therefore, understood that the service life until the initiation of cracking in Alloy 182 is considerably shortened by the addition of 0.1% NaCl (equivalent to 0.6 wt. % in terms of Cl concentration).

Figure 21:
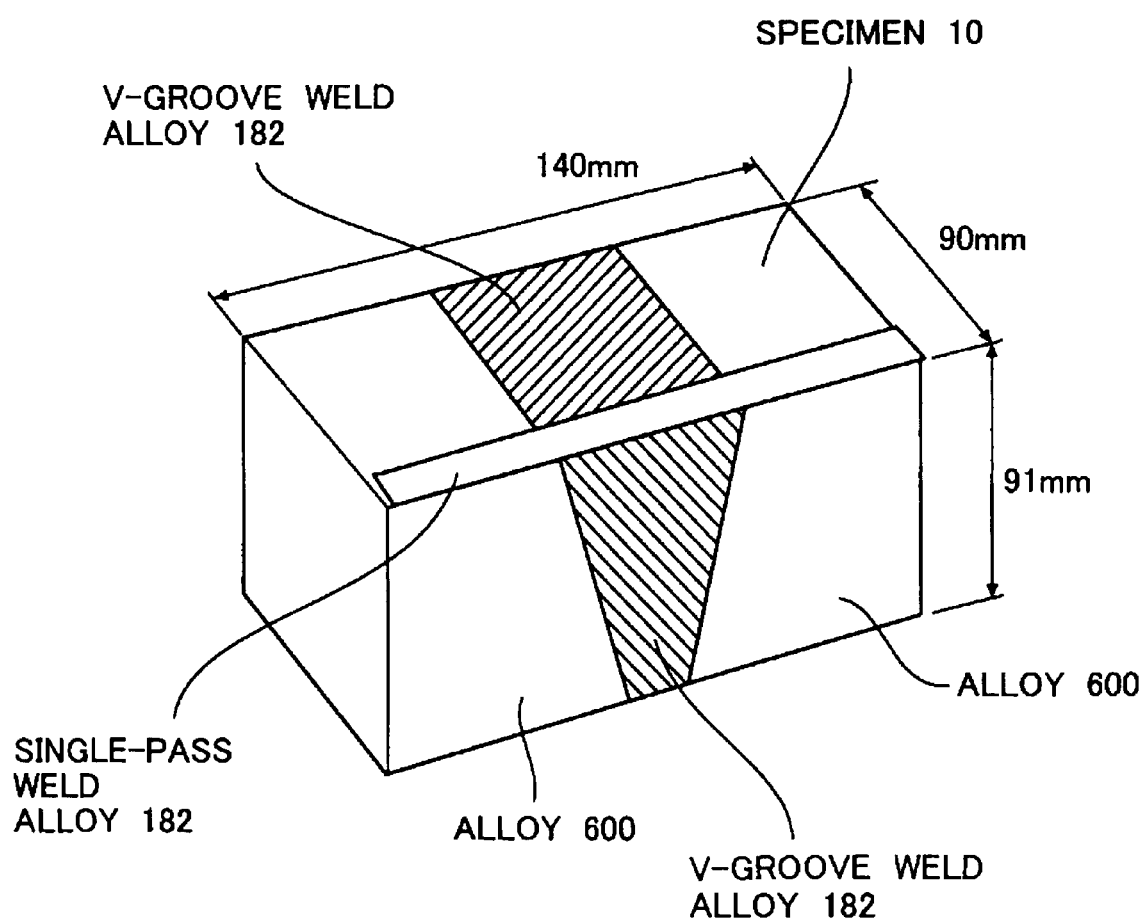
FIG. 21 is a perspective view of a specimen.

FIG. 21 is a perspective view for describing the shape and material of a specimen according to an embodiment of the present invention. The specimen 10 was prepared by cutting a V-groove in an approximately central part of a member 11, which was 91 mm in thickness and was made of Alloy 600, and welding the member with Alloy 182. The drawing shows a V-groove weld 12 and a single-pass weld 13. This specimen 10 was subjected to heat treatment at 600° C. for 24 hours and low-temperature aging at 500° C. for 24 hours. The arrangement of the single-pass weld 13 (a single-pass weld bead of Alloy 182) in the specimen 10 of FIG. 16 was to produce a welding residual stress under the welding conditions without any modification thereto. The single-pass Alloy 182 was formed from a welding consumable the stabilization parameter of which was not greater than 8, and was in a sensitized state after the welding without needing any further treatment.

Figure 22:
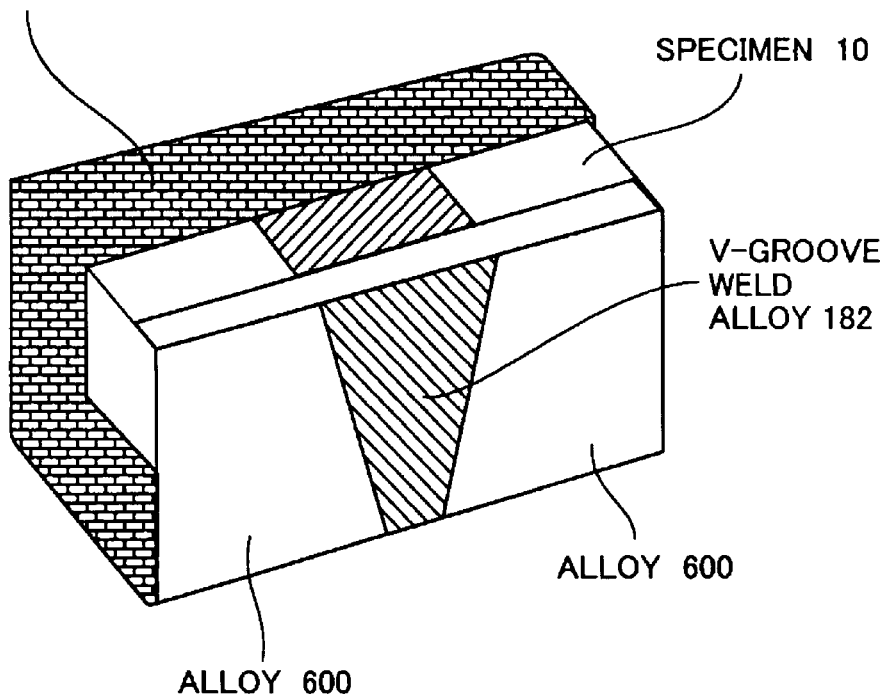
FIG. 22 is a perspective view of a specimen in a form coated with silicone rubber.

FIG. 22 is a view showing a specimen 10 with a silicone rubber coating 3 applied to an area other than an area where initiation of IGSCC was intended. This specimen allows to specifically limit an area where IGSCC is to be initiated.

FIG. 23 is a table showing two kinds of test conditions and the test results. In these two kinds of tests, the test solutions both met the conditions according to the present invention. Test No. M1 was a 144-hour test conducted after the surface of the specimen was ground by a grinder, while Test No. M2 was a 168-hour test after the surface of the specimen was buffed. The grinding and buffing were conducted to investigate how they would affect the welding residual stresses which inherently existed in the specimens. As a result of the tests, IGSCC were found to occur in both of the tests.

FIG. 24 is a view depicting a test arrangement in which a welded specimen 10 was tested in a container 14 made of polytetrafluoroethylene [tradename: TEFLON (trademark)]. It was a liquid penetrant test conducted by placing the specimen 10 in the container 14, pouring a (1 wt. %) aqueous solution 15 of $K_2S_4O_6$, and immersing the specimen 10 for a predetermined time in the aqueous solution 15.

Figure 25:
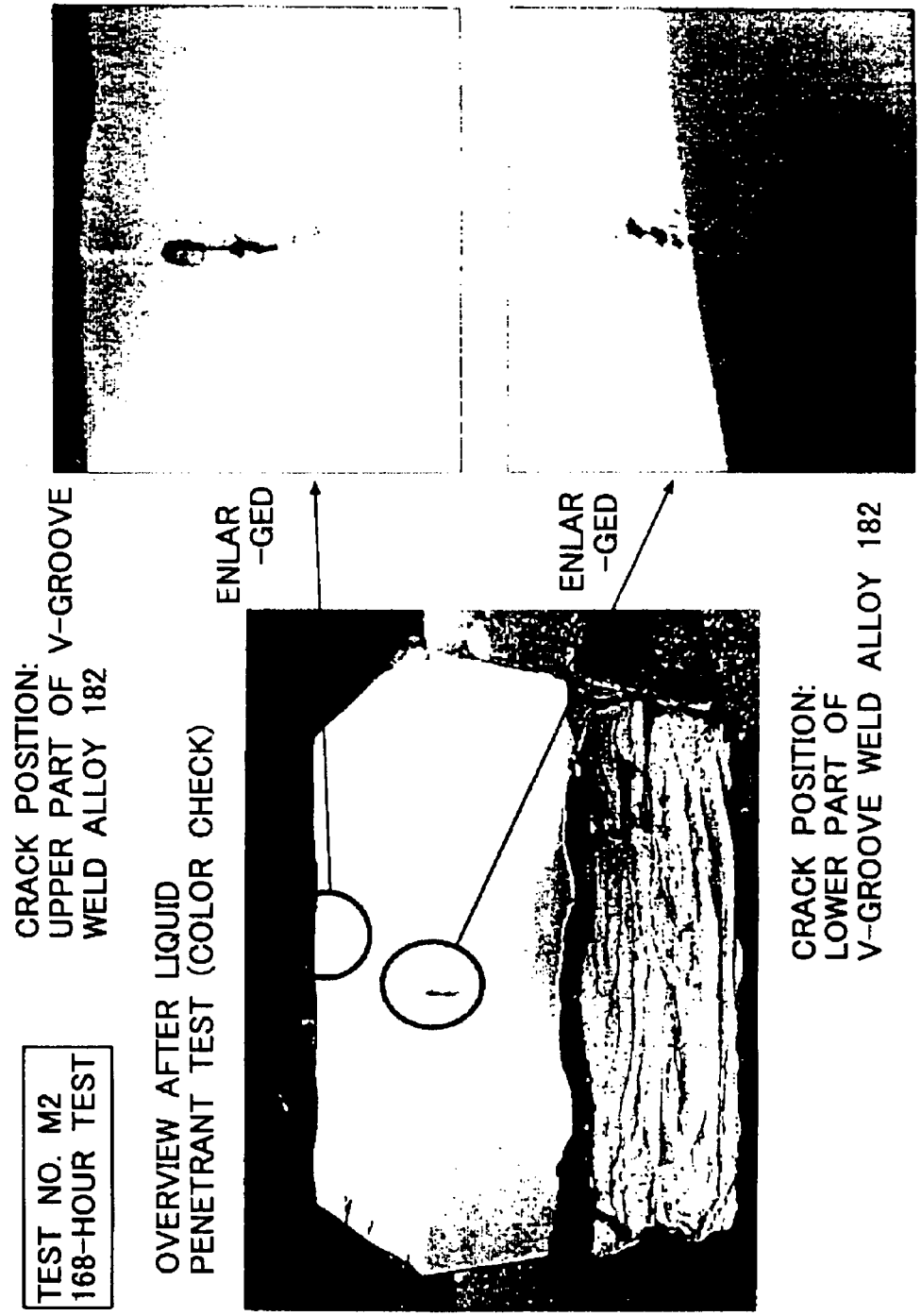
FIG. 25 shows photographs, which present details of cracking in a test piece.

FIG. 25 shows photographs, which present the results of the penetrant test of the specimen after the immersion test (see FIG. 24) conducted under the conditions of Test No. 2 shown in FIG. 23. FIG. 25 shows the positions of cracks in the circled areas, and also shows the enlarged details of the cracks.

Figure 26:
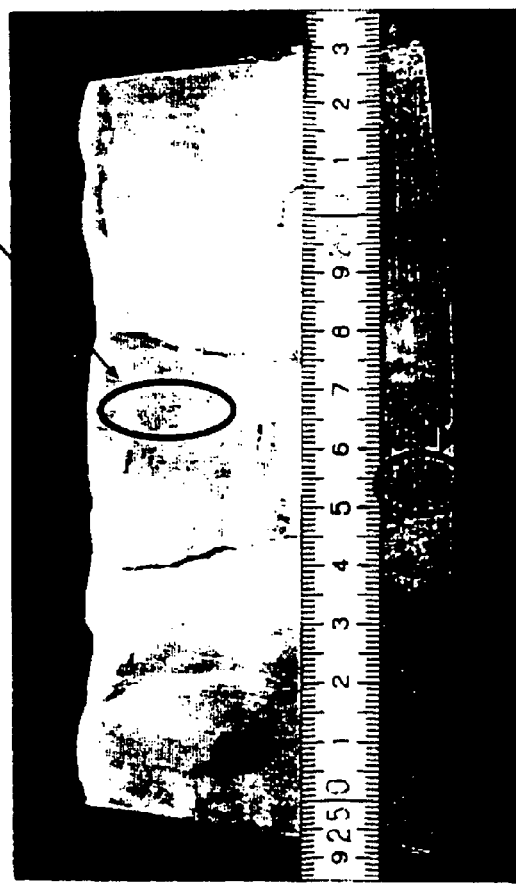
FIG. 26 shows a photograph and a simplified view, which present details of cracking in a test piece.
Figure 27:
FIG. 27 is a photograph showing conditions of a fracture surface of a test piece.

FIG. 26 is a photograph, which confirmed the detection of cracks on the side of a cross-section (a side wall) of the V-groove weld 12 after the specimen was washed and etched subsequent to the liquid penetrant test. One of the cracks so occurred was about 5 m in length (in a lower part of the V-groove weld), and the other was about 10 mm in length (in an upper part of the V-groove weld). FIG. 27 is a photograph of the IGSCC observed on a fracture surface, and confirms that the cracks observed in FIG. 25 are IGSCC.

As apparent from FIG. 25, no cracks initiated in the single-pass weld bead of Alloy 182. It has hence been found that, even when the stabilization parameter is not greater than 12, cracking hardly takes place if stress is small. It has also been found that IGSCC does not initiate at all under the welding conditions of the present invention.

FIG. 28 shows views of further welded specimens ① and ②, each of which was prepared by welding a member 11 of Alloy 600 and a member 16 of an austenite stainless steel together with a weld 12 of Alloy 182. These welds 12 of Alloy 182 become target areas for the initiation and growth of IGSCC. IGSCC can be caused to initiate by exposing these specimens 10 to a solution of the present invention in a container as shown in FIG. 24 either as are or after covering them with a non-metallic material such as a silicone rubber at areas other than the target areas for the examination of IGSCC initiation.

Figure 29:
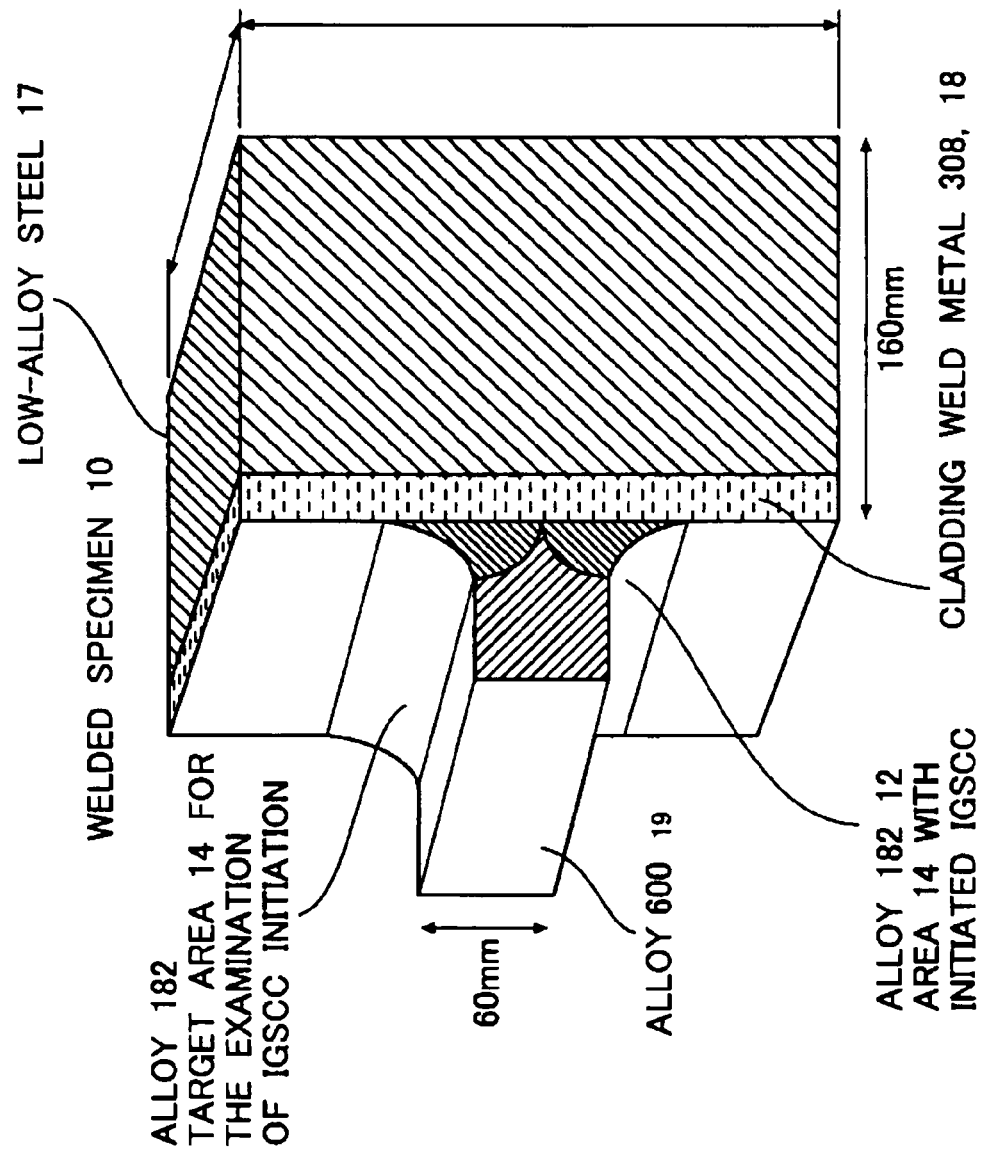
FIG. 29 is a perspective view of a still further specimen.

A still further, simulated specimen 10 depicted in FIG. 29 was prepared by forming a cladding weld overlay 18 of Stainless Steel 308 on low-alloy steel 17 and welding a nickel-based alloy (Alloy 600) 19 on the cladding weld overlay via welds 12 of Alloy 182. As the specimen 10 is large and is made of the low-alloy steel 17 in this case, a dam is formed with TEFLON-made, plate-shaped solution-holding members 20 and a sealing material of silicone rubber around the welds 12 of Alloy 182, which are the target areas for the initiation and growth of IGSCC, as illustrated in FIG. 30, and a test solution is then poured into the dam to immerse the welds 12 of Alloy 182.

Figure 30:
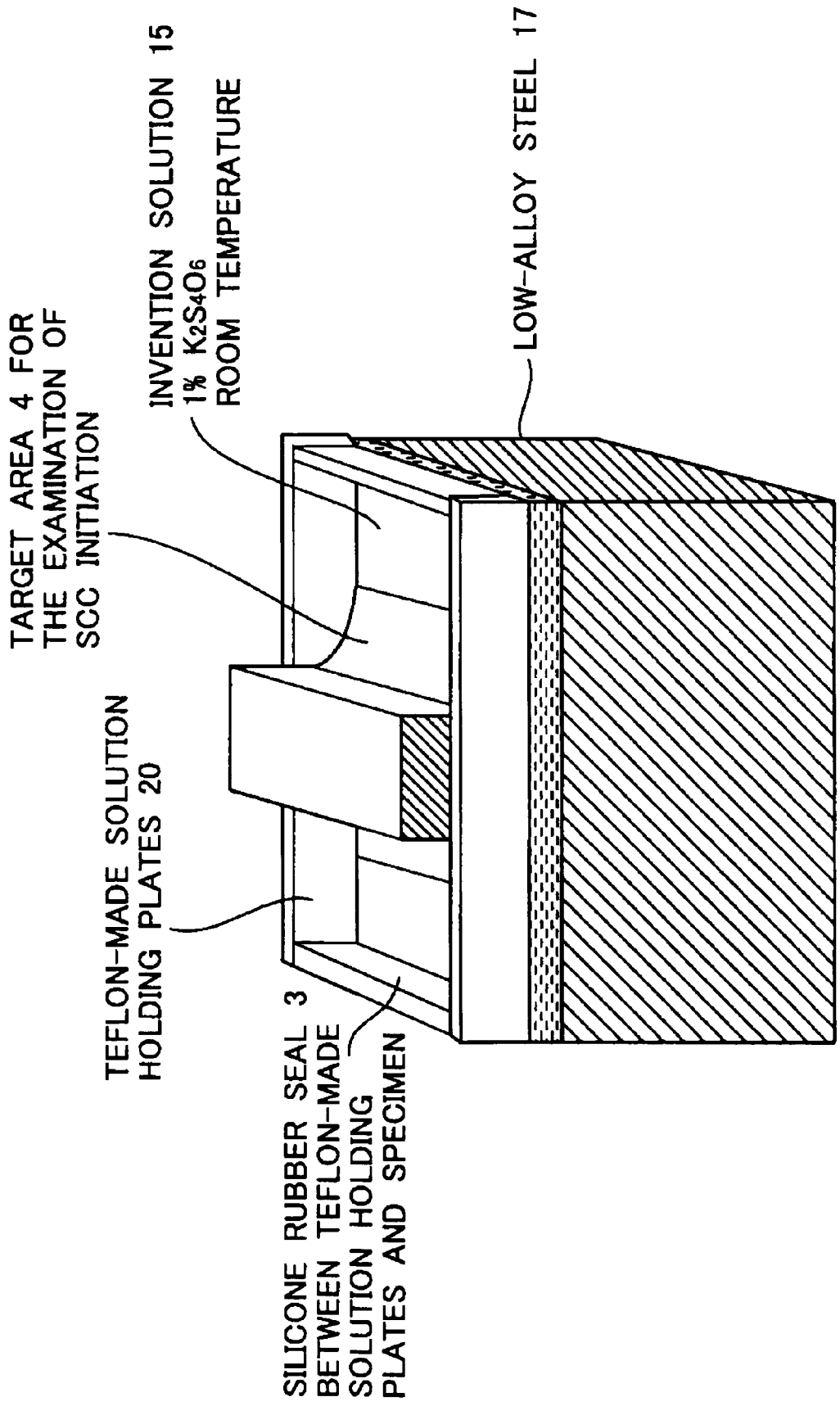
FIG. 30 is a view illustrating a yet further specimen under testing.
Figure 31:
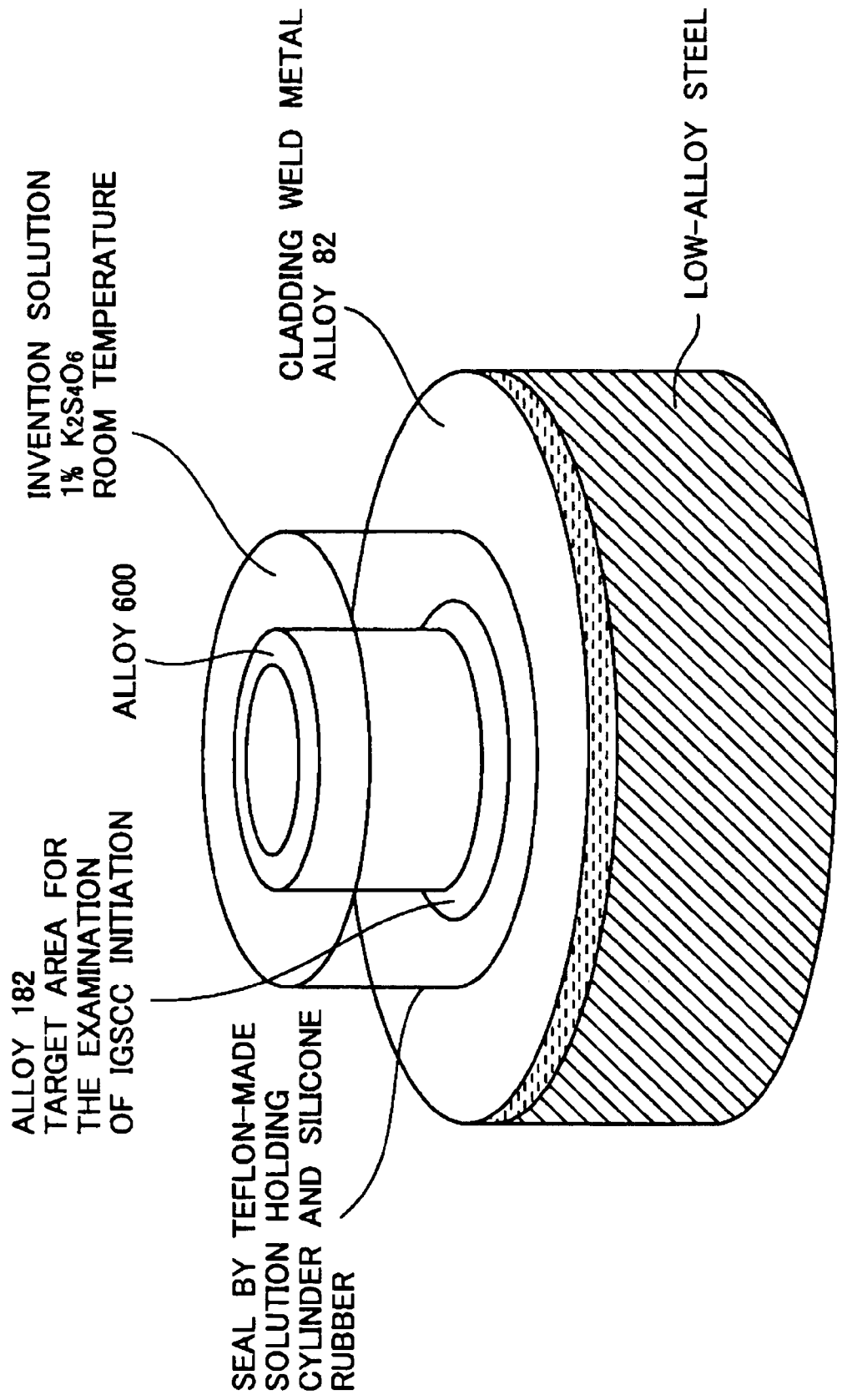
FIG. 31 is a view showing a still yet further specimen under testing.

FIG. 30 is a view illustrating a modification of FIG. 31. In this modification, a cylindrical solution-holding member 20 is used to surround the circumference of a weld 12 of Alloy 182. If necessary, external force can be applied to the specimen to facilitate the initiation of stress corrosion cracking.

Aqueous solutions of $K_2S_4O_6$ were used as test solutions in the above-described embodiments. The present invention is, however, not limited to them, and solutions of other tetrathionate salts, for example, aqueous solutions of $Na_2S_4O_6$ are also usable.

The technique of the present invention has made it possible to specifically limit an initiation area of IGSCC, and therefore, is very useful in technologically improving, for example, the equipment and methods for ultrasonic examination tests and eddy-current examination tests. As a method for specifically limiting an initiation area of IGSCC, it has already been mentioned to cover an area other than the initiation area with a non-metallic material such as rubber or resin. It is, however, necessary to cover a wide area with a non-metallic material when an area where IGSCC may initiate is broad although IGSCC is desired to initiate in only an extremely small part of the area.

A description will next be made about a testing method which allows a user of a specimen to simply and easily cause IGSCC to initiate at a desired position in a manner other than the above-described coating. Although it is effective to specifically limit an initiation area of IGSCC by coating, there is a potential problem that a flow of ions or the like indispensable for the initiation of SCC may be blocked by the coating. It is, therefore, difficult to specifically limit an area, which is to be brought into contact with a test solution, to a very small area. In contrast to the above-described method, the testing method to be described next is free of such a potential problem, allows IGSCC to initiate and grow well, and also, makes it possible to specifically limit an area, which is to be brought into contact with a test solution, to a very small area.

This method is characterized in that after preparation of a welded structure, in other words, after welding a structure, the structure is mechanically ground or polished by a grinder or buff at the weld bead only in an area where the initiation of IGSCC is desired and the weld bead in the remaining area is left unground or unpolished, and in this state, the structure is immersed in a $K_2S_4O_6$ solution to cause IGSCC to initiate and grow. The area where the surface has been ground by the grinder or the like serves as an area having a high potential for the initiation of IGSCC, thereby making it possible to cause IGSCC to preferentially initiate at the specific area.

Figure 32:
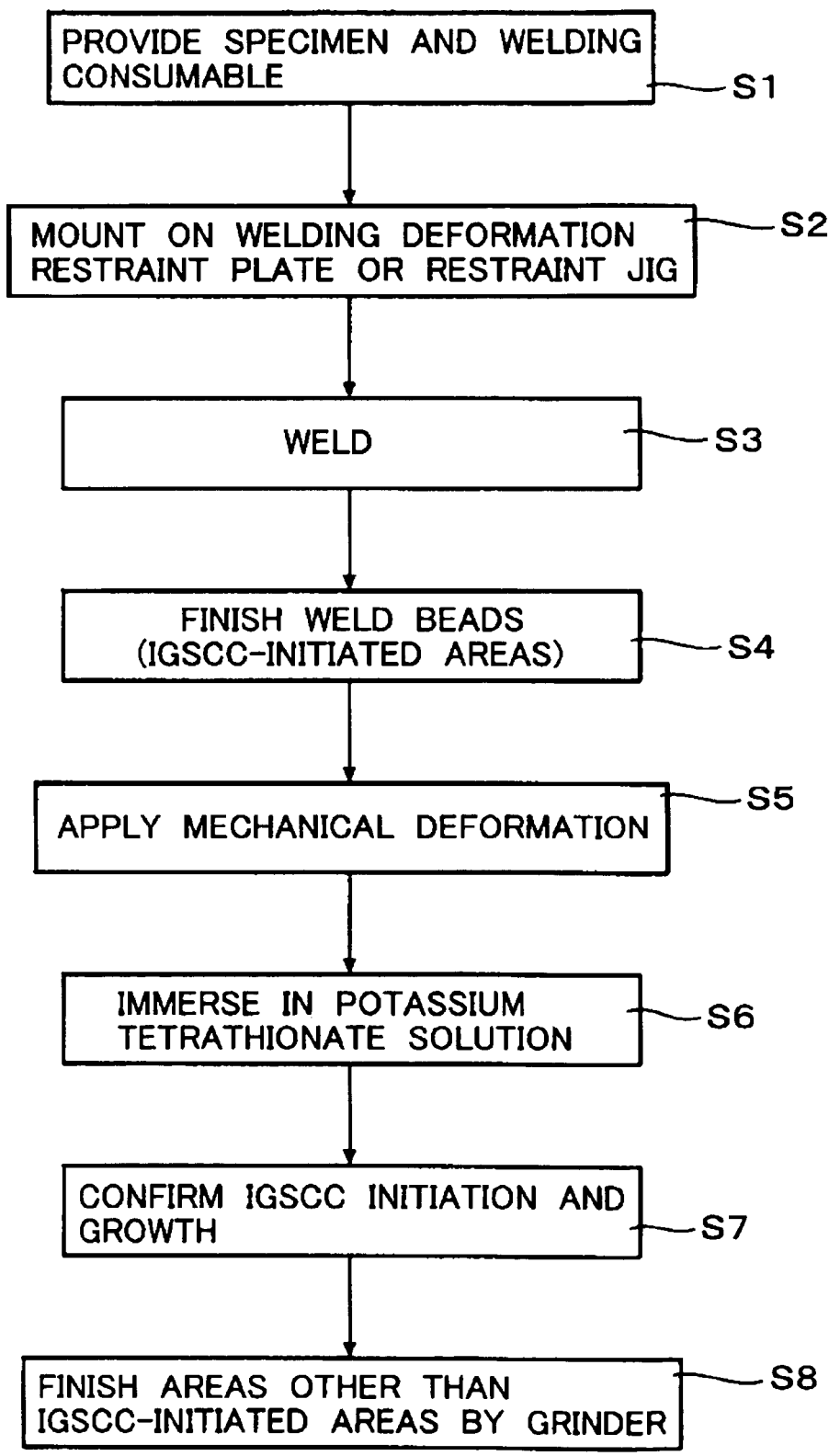
FIG. 32 is a flow chart of a first testing method.

FIG. 32 is a flow chart of a first testing method. In S1, a plate-shaped specimen made of a metal capable of retaining corrosion resistance through passivation, for example, a nickel-based alloy or the like and a welding consumable made, for example, of a nickel-based alloy are provided (S1).

The specimen is mounted on a welding deformation restraint plate or restraint jig (S2), and is welded in the mounted state (S3). Subsequent to the welding, a bead is ground and finished by a grinder or the like only at an area where the initiation of IGSCC is desired in S4. In S5, the specimen is set on a deformation applying jig the upper surface of which is bulged in a slightly curved form as shown in FIG. 6B, and is tightened by bolts and nuts to apply a mechanical deformation thereto. Although the mechanical deformation was applied by bending in this embodiment, the mechanical deformation can also be applied in a different manner, for example, by pulling or the like.

Subsequently, the specimen is immersed for a predetermined time in an aqueous solution of $K_2S_4O_6$ (S6). After the specimen is pulled out of the solution and the initiation and growth of IGSCC are confirmed (S7), the specimen is ground and finished by a grinder or the like at the area other than the area where IGSCC has initiated (S8).

In this testing method, the welding can be directly conducted by omitting the mounting of the specimen on the welding deformation restraint plate or restraint jig in S2. Further, the specimen can be directly immersed in the aqueous solution of $K_2S_4O_6$ by omitting the application of the mechanical deformation to the specimen in S5.

Figure 33A:
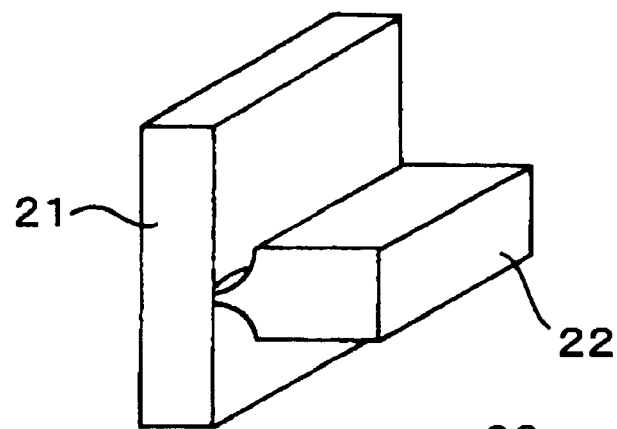
FIGS. 33A through 33D are perspective views, which specifically illustrate the testing method making use of a grinding means.
Figure 33B:
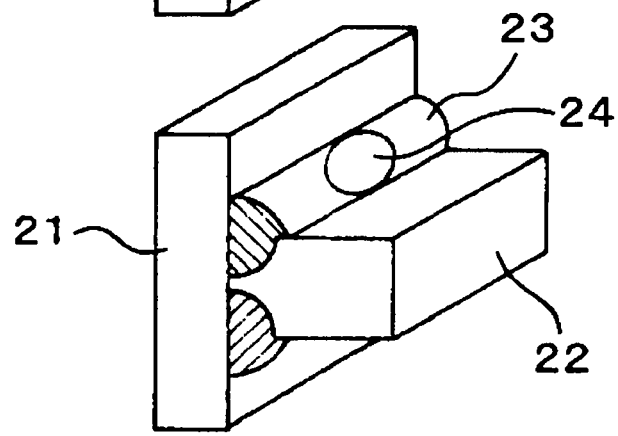

FIGS. 33A through 33D are perspective views, which specifically illustrate the testing method making use of the grinding means. As depicted in FIG. 33A, a simulated support plate 22 made of Alloy 600 is brought at a free end thereof into abutment against a side wall of a simulated support cylinder 21 made of Alloy 600, and as illustrated in FIG. 33B, they are welded together. One of the thus-formed weld beads 23 is ground by a grinder at an area where IGSCC is intended to initiate, so that a ground part 24 is formed to provide a specimen.

Figure 33C:
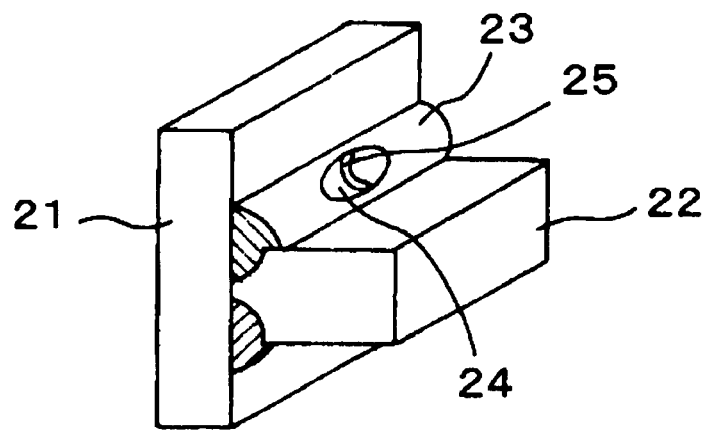
Figure 33D:
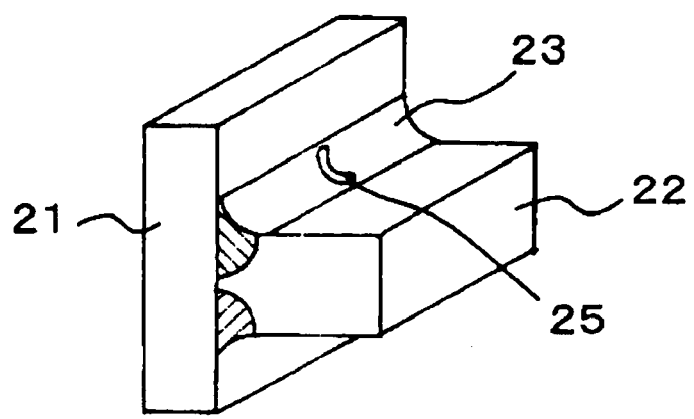

This specimen is immersed for a predetermined time in the above-mentioned test solution such that IGSCC 25 is caused to initiate and grow as shown in FIG. 33C. After confirming it, the weld bead 23 is ground and finished in its entirety by a grinder as shown in FIG. 33D.

Figure 34:
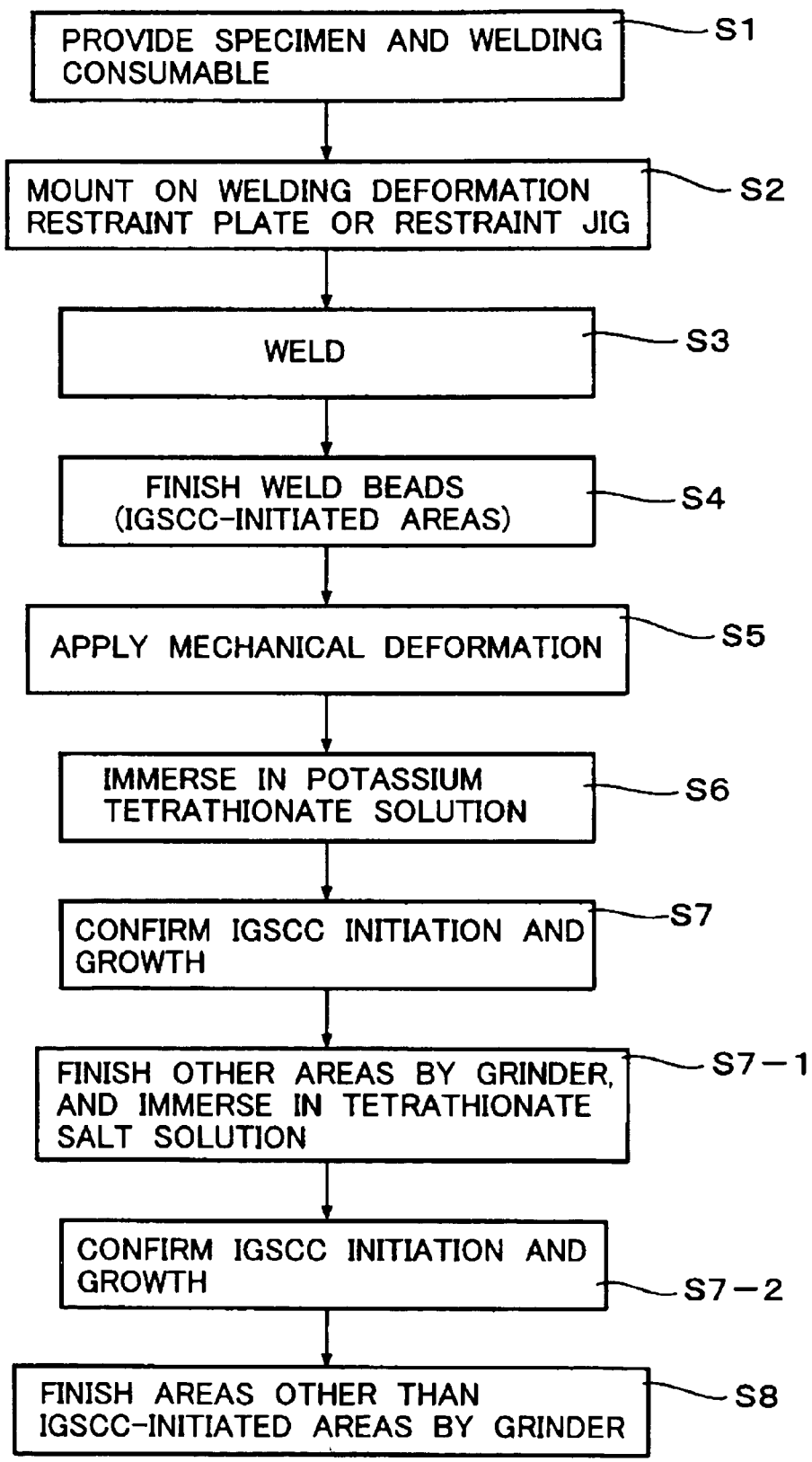
FIG. 34 is a flow chart of a second testing method.

FIG. 34 is a flowchart of a second testing method. This flow chart is different from the flow chart shown in FIG. 32 in that, after the initiation and growth of IGSCC have been confirmed in S7, the weld bead is ground and finished at the remaining area thereof by a grinder or the like and is immersed in the aqueous solution of $K_2S_4O_6$ to cause new IGSCC to initiate and grow in S7-1 and the new IGSCC is confirmed in S7-2. By this method, IGSCC can be caused to initiate and grow on a single specimen at plural areas with a time interval.

Figure 35:
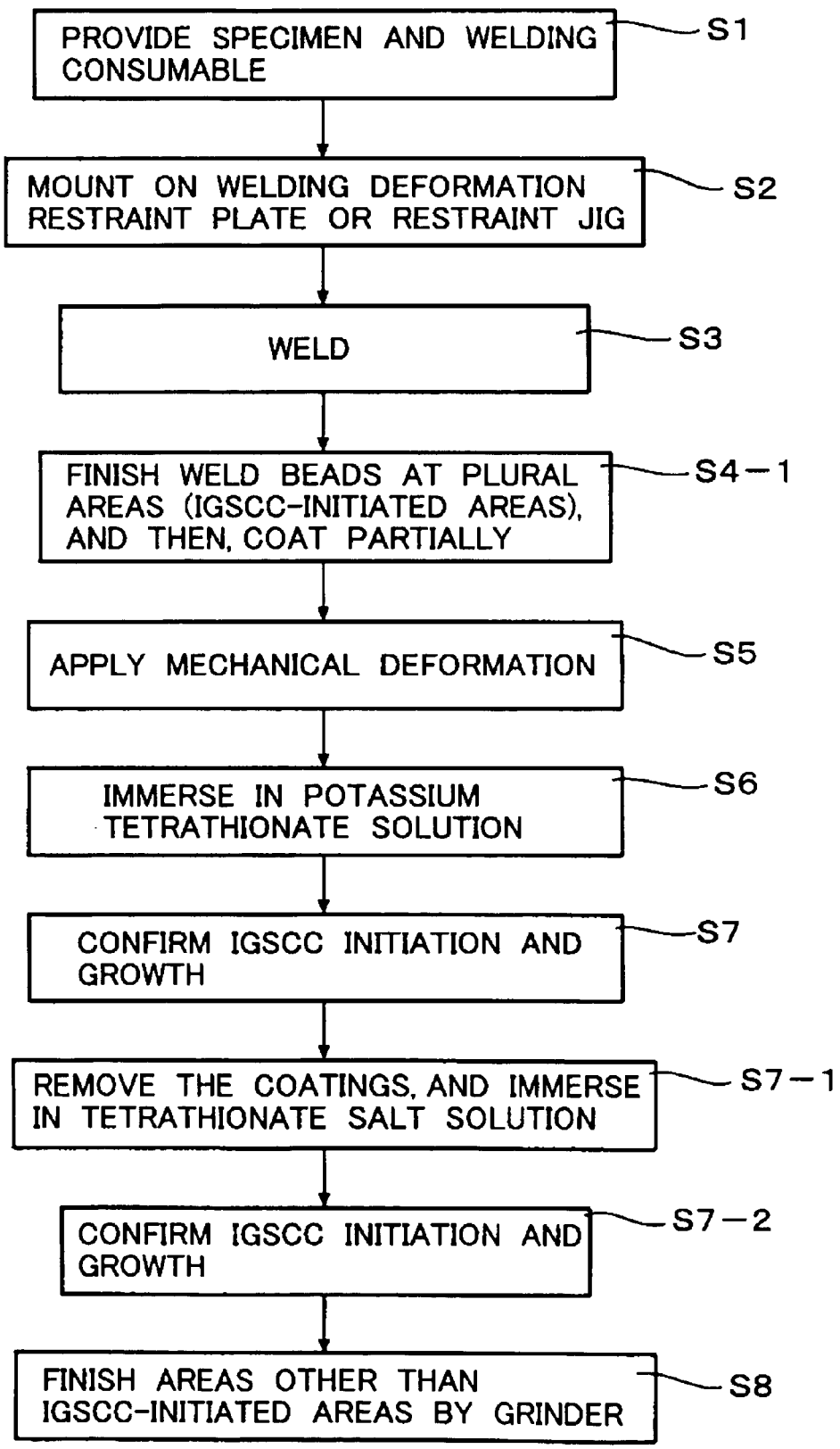
FIG. 35 is a flow chart of a third testing method.

FIG. 35 is a flow chart of a third testing method. This flow chart is different from the flow chart shown in FIG. 32 in that, after welding in S3, the weld bead is ground and finished at plural areas thereof by a grinder or the like and is partially coated with a non-metallic material in S4-1 and also in that, after the initiation and growth of the first IGSCC have been confirmed in S7, the above-mentioned coating is removed and the specimen is immersed again in the aqueous solution of $K_2S_4O_6$ to cause new IGSCC to initiate and grow and the new IGSCC is confirmed in S-7. By this method, IGSCCs can be caused to initiate and grow with different contact time periods with the aqueous solution of $K_2S_4O_6$.

Figure 36:
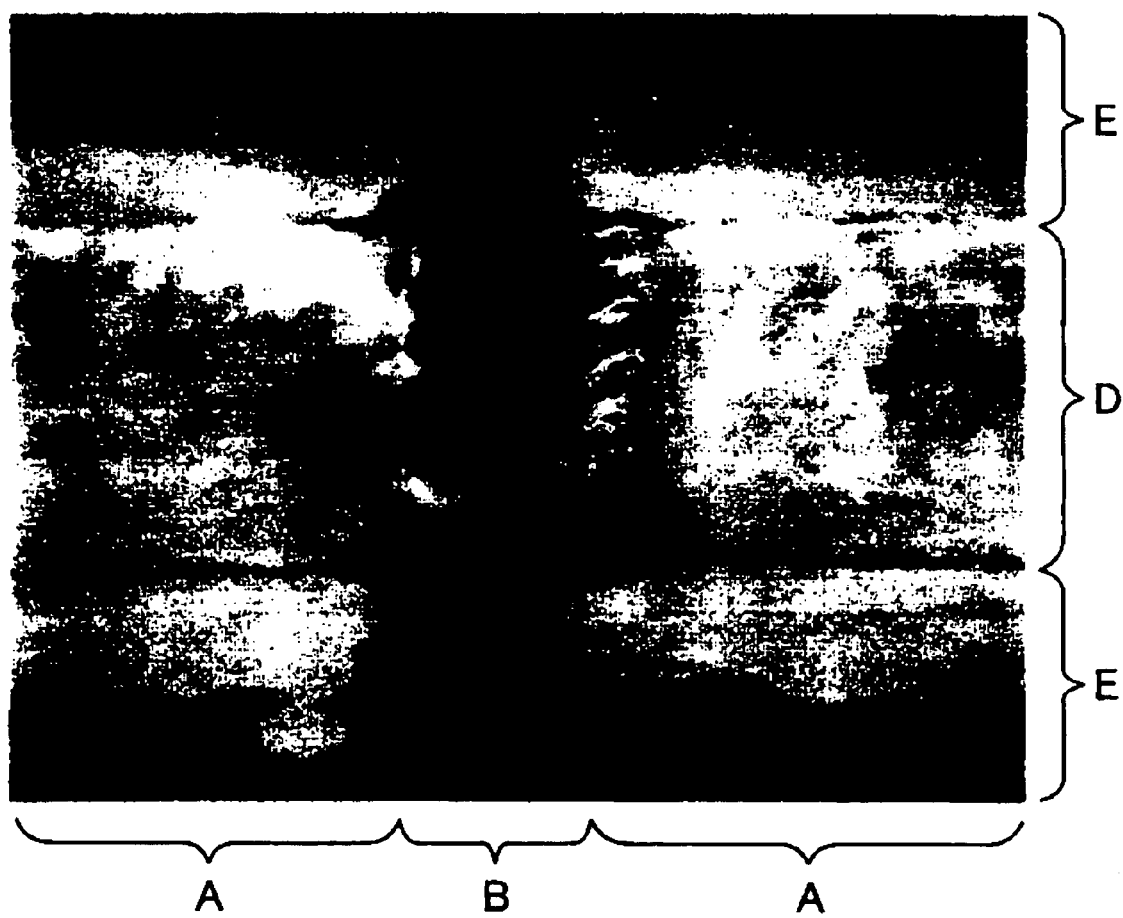
FIG. 36 is a photograph of a specimen, which shows a grinder-finished area and grinder-unfinished area of a weld bead.

FIG. 36 is a photograph of a specimen. The photograph shows areas A and an area B of a weld bead, which were grinder-finished and grinder-unfinished, respectively, after Alloy 600 (portions indicated by letter E in the figure) was welded with Alloy 182 (a portion indicated by letter D in the figure).

Figure 37:
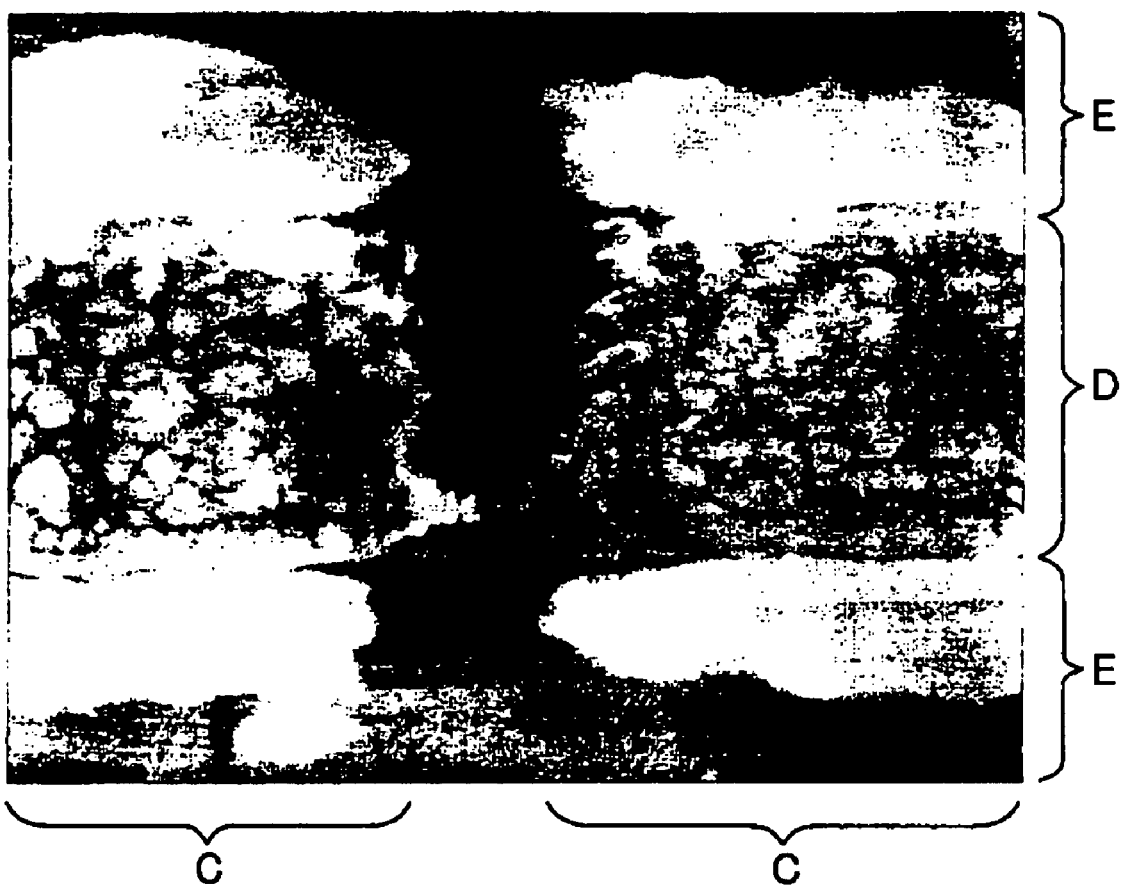
FIG. 37 is a photograph showing that patterns of IGSCC had been detected on the specimen.

FIG. 37 is a photograph showing that patterns C were detected at the grinder-finished areas A by immersing the specimen in the aqueous solution of $K_2S_4O_6$ and conducting a penetrant examination after the immersion. It has been found from the detection that IGSCC preferentially initiates and grows at a grinder-finished area.

Because Alloy 600 having good corrosion resistance was used as a base metal in the specimen, IGSCC did not initiate in Alloy 600 under the above-described immersion conditions.

Figure 38:
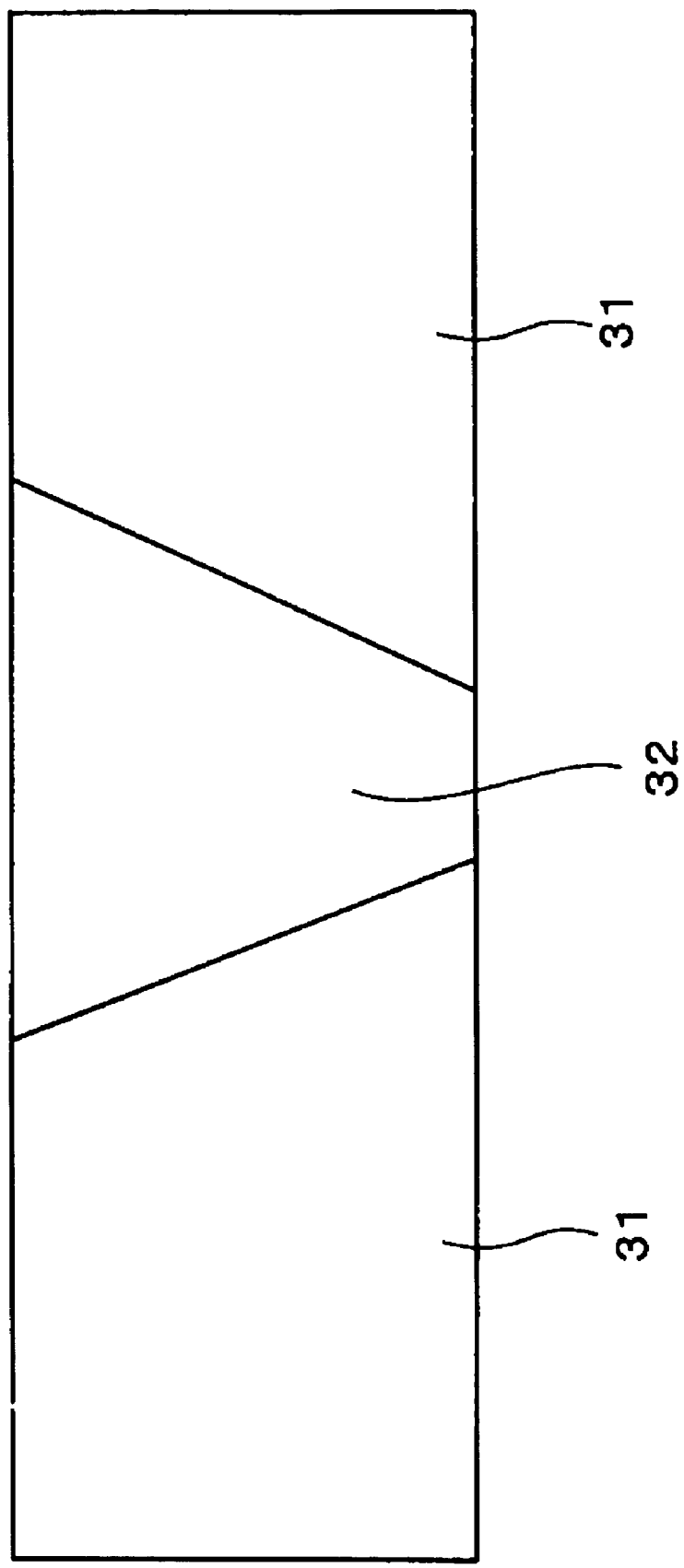
FIG. 38 is a simplified view showing an illustrative welded joint in an in-core structure of a pressure vessel.

A description will next be made about sensitization treatment of a specimen. FIG. 38 is a simplified view showing an illustrative welded joint (welded structure) in an in-core structure of a pressure vessel in a nuclear power plant. The figure shows stainless steel base metals 31 joined together via a weld metal 32 of ferrite-containing austenite stainless steel. To perform maintenance against SCC in a weld of such a structure, a technique is needed to cause IGSCC to initiate and grow on specimens.

FIG. 39 is a table showing an illustrative chemical composition of the weld metal 32 of ferrite-containing austenite stainless steel. In the case of this material, the content of ferrite is 8 vol. %. Those having a ferrite content of from 8 to 15 vol. % are generally used. FIG. 40 is a table showing illustrative welding conditions (welding rod diameter, current, voltage, welding speed, heat input, interlayer temperature) upon preparing a specimen.

Figure 41:
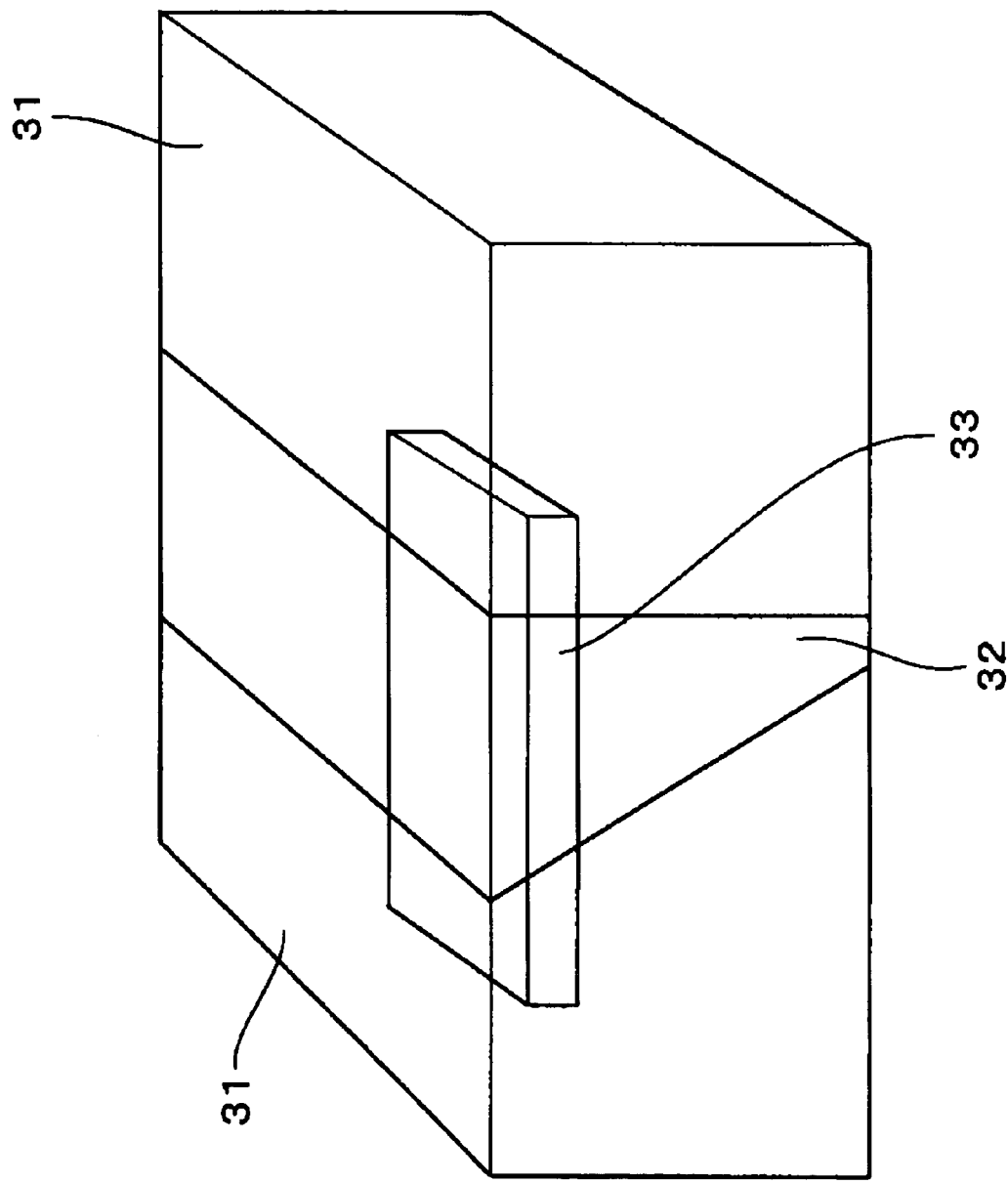
FIG. 41 is a diagram illustrating how to cut out the specimen.

FIG. 41 is a diagram illustrating how to cut out, from the welded structure shown in FIG. 38, a cut-out specimen 33 with the weld metal 32 of ferrite-containing austenite stainless steel included therein. This cutout specimen 33 has a V-groove weld in a substantially central part thereof.

To such specimens 33, heat treatment was applied at 610° C. for 6 hours to 40 hours, respectively, as illustrated in FIG. 42. On the specimens subjected to the heat treatment, a modified ASTM A262E test shown in FIG. 43 was conducted. Test conditions were as shown in the same figure.

Figure 44:
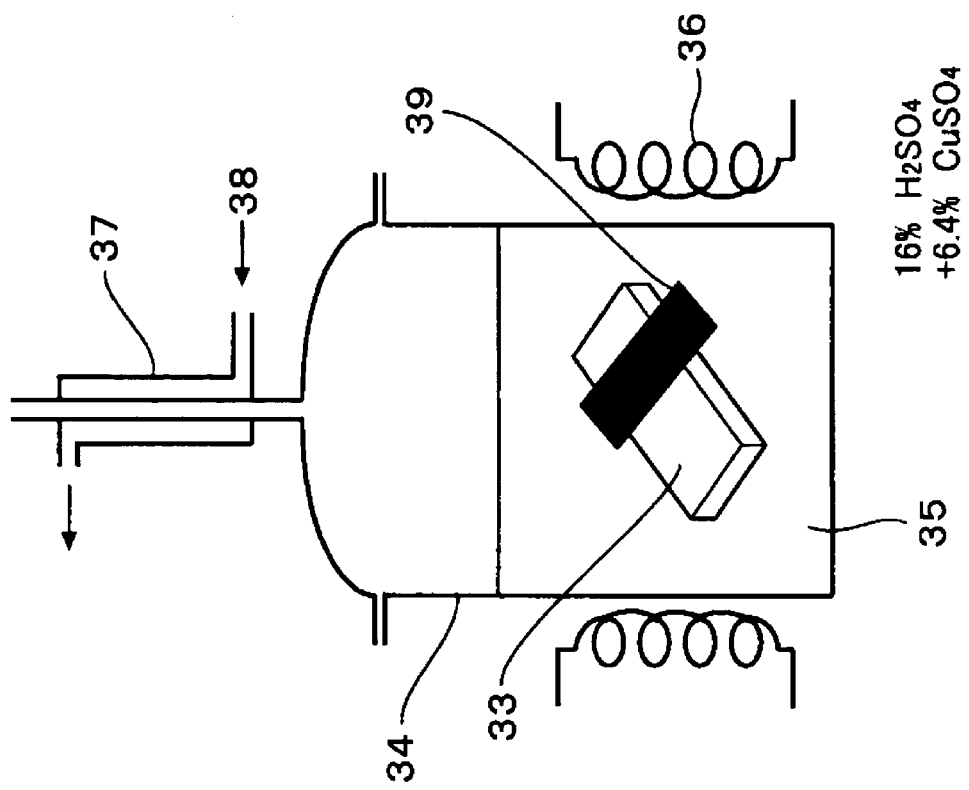
FIG. 44 is a simplified construction diagram showing the arrangement for a test by the modified ASTM A262E method.

FIG. 44 is a simplified construction diagram of the test apparatus. As illustrated in the diagram, a test solution 35 (16% $H_2SO_{4+6.4}$% $CuSO_4$) for the modified ASTM A262 test is placed in a test container 34, the above-mentioned specimen 33 is immersed in the test solution 35, and then, the test solution 35 is heated and boiled by a heater 36. Generating steam is condensed into dew with cooling water 38 fed through a condenser tube 37, and water droplets are allowed to return to the test container 34. In the modified ASTM A262E test, it is stipulated to conduct the test with a copper piece 39 kept in contact with the specimen 33.

Figure 45:
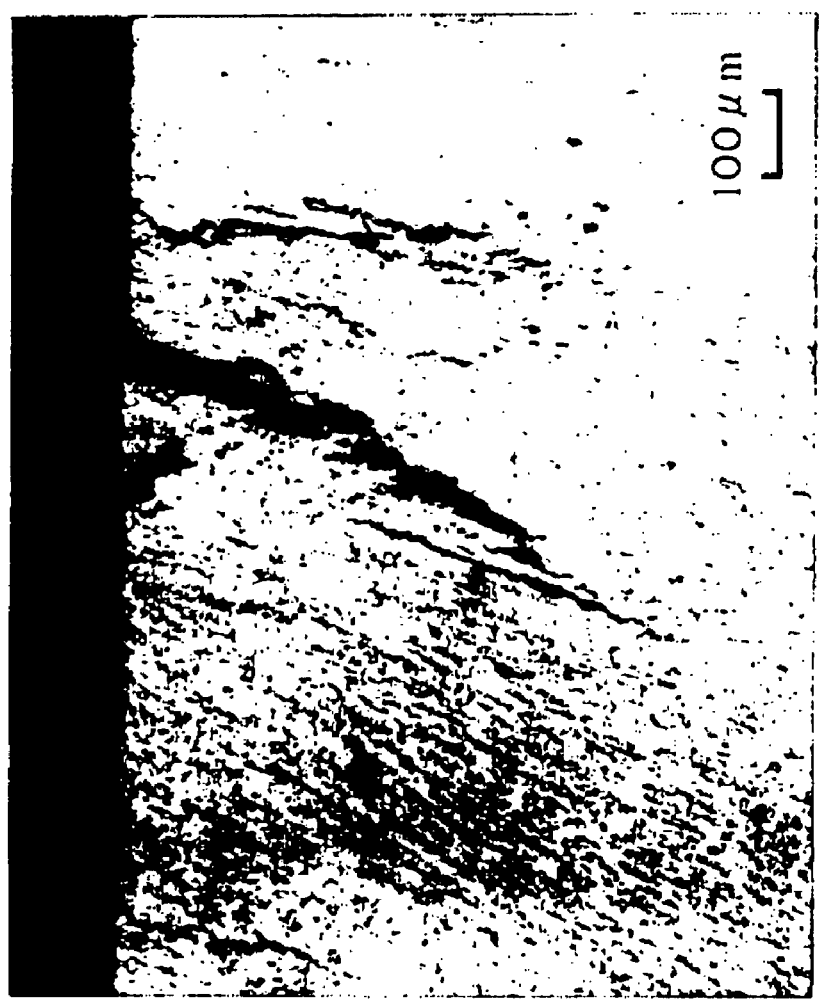
FIG. 45 is a photograph showing a cross-section of the specimen after the test by the modified ASTM A262E method.

FIG. 45 is a photograph showing a cross-section of the specimen 33 after the modified ASTM A262E test of the weld metal of ferrite-containing austenite stainless steel, which had been subjected to heat treatment at 610° C. for 6 hours (the heat treatment conditions No. 1 in FIG. 42), was conducted. It is understood from this photograph that the specimen 33 had developed intergranular corrosion.

Figure 46:
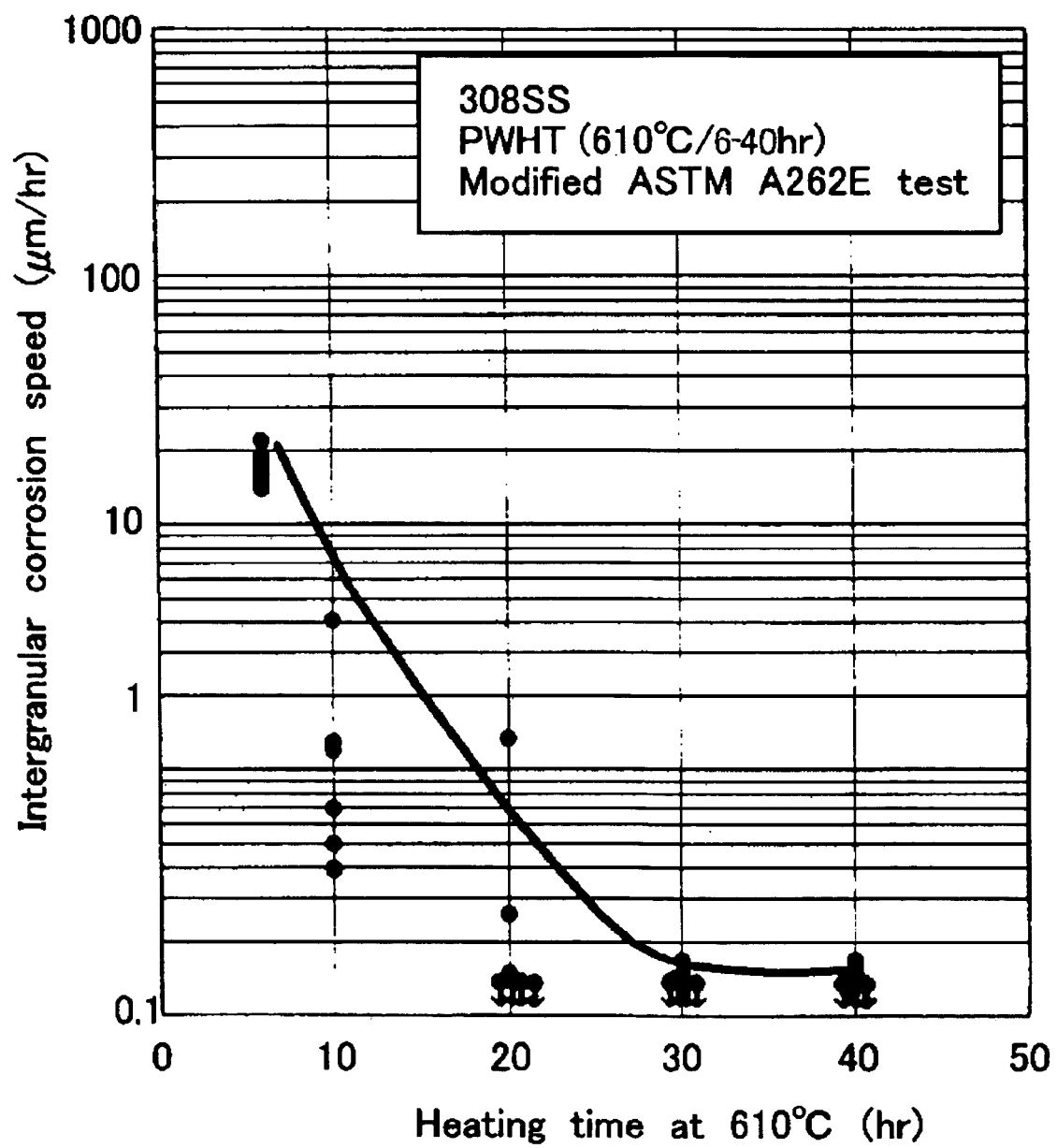
FIG. 46 is a graphic diagram of heating time versus intergranular corrosion speed as determined by the modified ASTM A262E method.

FIG. 46 is a characteristic diagram showing the behavior of intergranular corrosion when heat treatment was applied to a weld metal of ferrite-containing austenite stainless steel at 610° C. for different periods in a range of from 6 hours to 40 hours. It is appreciated from the diagram that by applying heat treatment to a specimen at 610° C. for 6 hours to 15 hours, substantial intergranular corrosion takes place to sensitize the specimen.

From the foregoing, it has been found that a specimen is sensitized when a weld metal of ferrite-containing austenite stainless steel is subjected to heat treatment at 610° C. for 6 hours to 15 hours. It was, therefore, investigated how the heat treatment time would vary in a temperature range of from 500 to 650° C. by making use of the activation energy for Cr diffusion which plays a role in the sensitization. The results of the investigation will be described hereinafter.

Heat treatment is applied to a specimen within the following temperature range:

$$500° C. \leq T° C. \leq 650° C.$$

and the following time range:

$$t_1 \text{ hours} \leq t \text{ hours} \leq t_2 \text{ hours}$$

where $$t_1 = 6\exp\left\{\frac{Q}{R}\left(\frac{1}{T+273} - \frac{1}{883}\right)\right\}$$

$$t_2 = 15\exp\left\{\frac{Q}{R}\left(\frac{1}{T+273} - \frac{1}{883}\right)\right\}$$

Q=50,000 to 60,00 cal/mol, and
R=1.987 $calK^{-1}mol^{-1}$.

By this heat treatment to the specimen, Cr-depleted layers are formed at boundaries between ferrite phases and austenite phases as a result of the deposition of Cr carbides so that the specimen can be sensitized.

The lower limit of the treatment temperature was set at 500° C., because the heat treatment time ranges from 346 to 865 hours when Q=50,000 cal/mol and the heat treatment time becomes excessively long at temperatures lower than 500° C. On the other hand, the upper limit of the treatment temperature was set at 650° C., because at temperatures higher than the lower limit, the concentration of Cr in the interfaces of Cr carbides becomes so high that sensitization can be hardly achieved. The activation energy Q for sensitization was set at 50,000 to 60,000 cal/mol by determining it from a range which the activation energy for Cr diffusion can take.

By bringing a specimen, which has been sensitized as described above, into contact with a $K_2S_2O_6$ test solution or a $NaCl+K_2S_2O_6$ test solution, IGSCC initiates well and the state of its growth can be observed.

Figure 47:
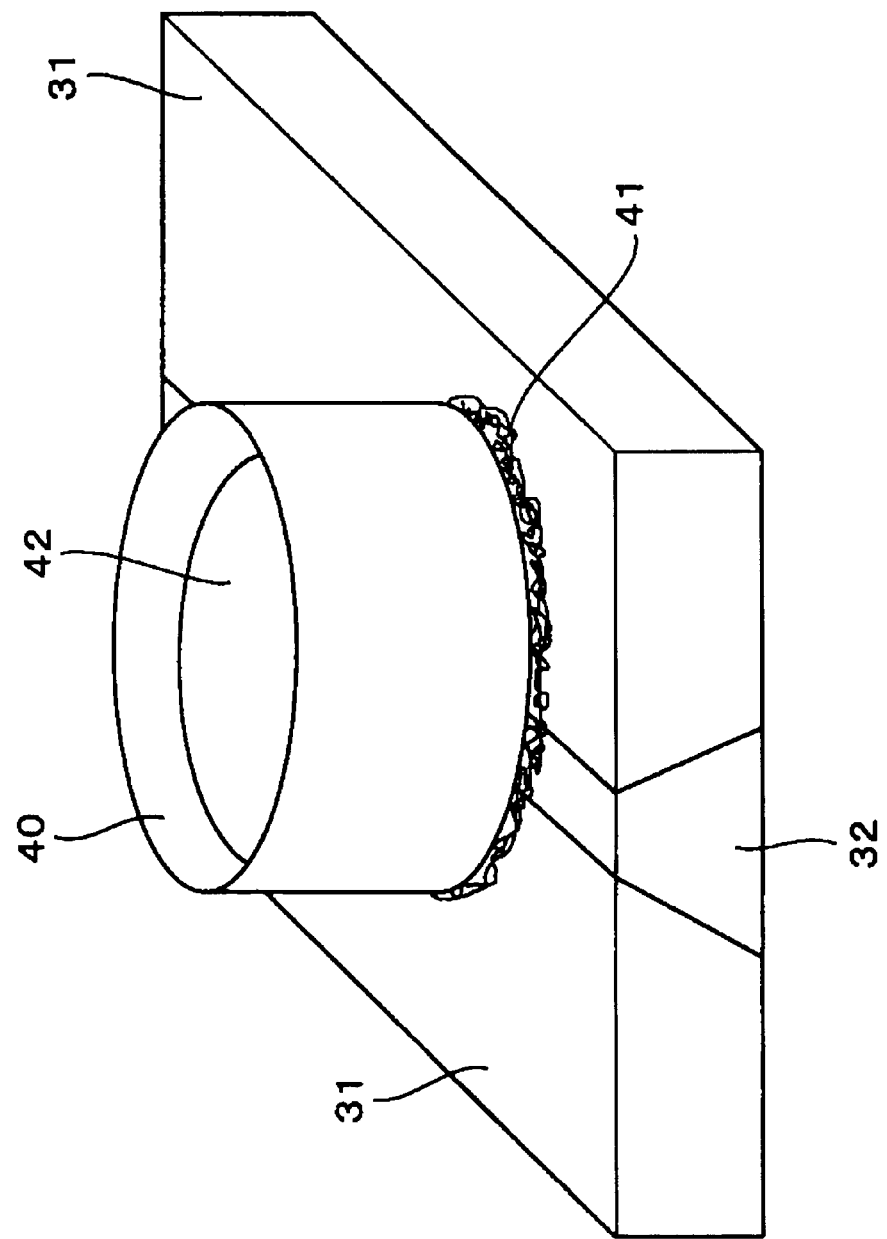
FIG. 47 is a perspective view showing how to test a sensitized specimen.

FIG. 47 is a perspective view showing an arrangement for the test. On a weld metal 32 of ferrite-containing austenite stainless steel, a container 40 which is open at the bottom thereof and is made of TEFLON, for example, is fixedly arranged with a silicone rubber 41. A test solution 42 consisting of the aqueous solution of $K_2S_4O_6$ or the aqueous solution of $NaCl+K_2S_4O_6$ was poured into the container 40 so that IGSCC is caused to initiate and grow in the weld metal 32.

Figure 48:
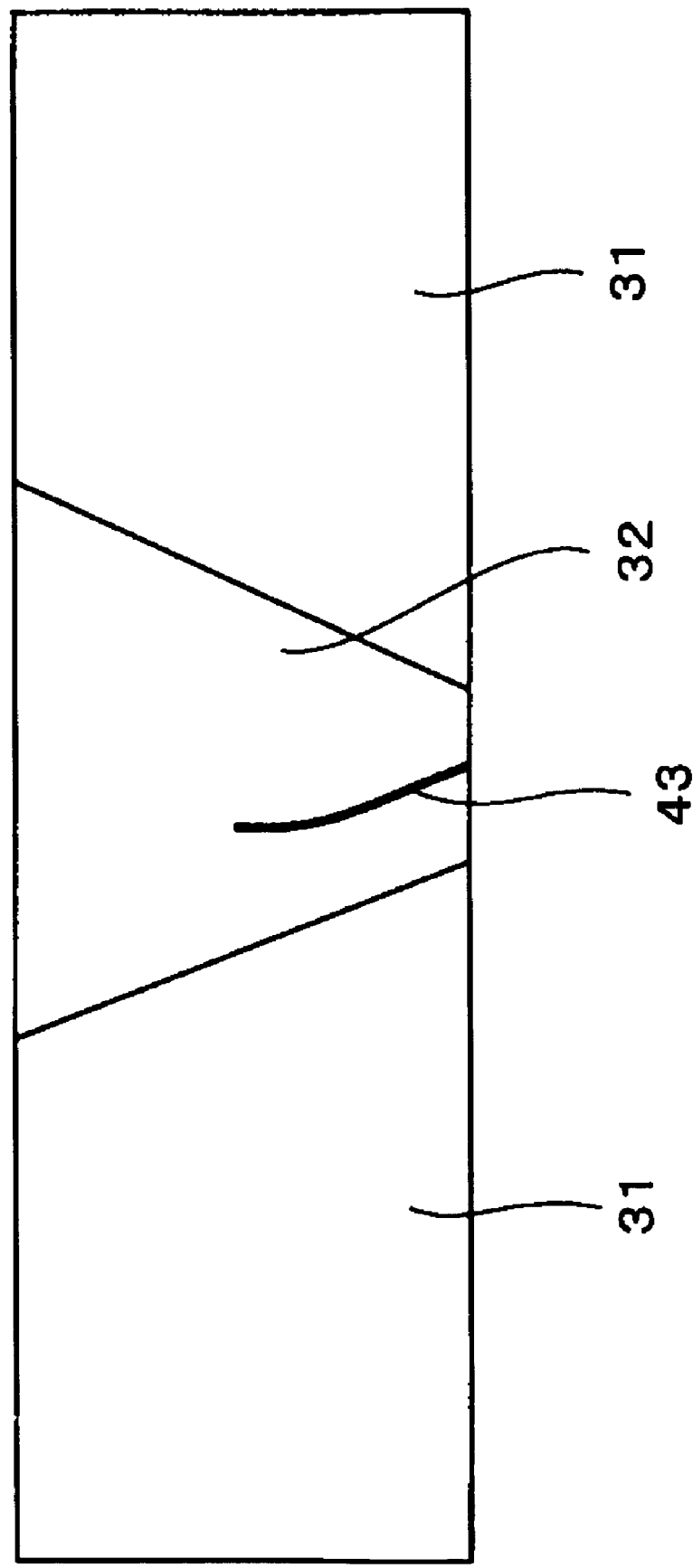
FIG. 48 is a simplified view showing the state of IGSCC initiated and grown in an austenite stainless steel weld metal.

FIG. 48 is a simplified view showing the state of an IGSCC 43 initiated and grown in the weld metal 32 of ferrite-containing austenite stainless steel.

The technique according to the present invention for the initiation and growth of IGSCC is useful in a variety of technical fields, for example, for purposes such as:

(1) improvements in UT technology,
(2) development of inspection techniques other than UT,
(3) development of repair techniques for Inconel structures,
(4) verification of reasonability of the results of a residual stress analysis of a welded structure by the elastoplastic analysis,
(5) empirical verification of an examination technique for potential SCC in a mockup specimen of a welded structure in actual equipment, and
(6) various surface treatment confirmation tests.

INDUSTRIAL APPLICABILITY

The first aspect of the present invention is characterized by bringing a specimen, which is made of a material capable of retaining corrosion resistance through passivation, into contact with a solution of a tetrathionate salt such that intergranular stress corrosion cracking initiates and grows in the specimen. It is, therefore, possible to simply and easily cause only IGSCC to initiate at atmospheric pressure in a short period.

The second aspect of the present invention is characterized in that the specimen is a welded structure or a simulated specimen of the welded structure, or a cut-out specimen cut out from the welded structure or the simulated specimen. It is, therefore, possible to determine the position and extent of initiated IGSCC in a short time in a laboratory under the conditions of the material of a structure in actual equipment or under welding residual stress in the structure.

The third aspect of the present invention is characterized by providing means for applying a strain to the specimen such that the specimen is brought into contact with the tetrathionate salt solution while being applied with a strain by the means. The fourth aspect of the present invention is characterized in that the means for applying a strain to the specimen is a weld applied to the specimen. Further, the fifth aspect of the present invention is characterized in that the means for applying a strain to the specimen is a member or device for applying a strain to the specimen from an outside. It is, therefore, possible to precisely determine the initiation and state of growth of IGSCC.

The sixth aspect of the present invention is characterized in that the solution of the tetrathionate salt is an aqueous solution of potassium tetrathionate or sodium tetrathionate, and a concentrate of potassium tetrathionate or sodium tetrathionate, a temperature of the solution and a pH value of the solution are controlled to a range of from 0.3 to 6 wt. %, a range of from 5 to 60° C. and a range of from 3 to 6, respectively. It is, therefore, possible to cause only IGSSC to surely initiate in the specimen.

The seventh aspect of the present invention is characterized in that the aqueous solution of potassium tetrathionate or sodium tetrathionate contains chlorine in a range of from 0.06 to 6 wt. %. Further, the eighth aspect of the present invention is characterized in a concentration of the chlorine is controlled to a range of from 0.6 to 6 wt. %. It is, therefore, possible to cause only IGSCC to more surely initiate in the specimen.

The ninth aspect of the present invention is characterized by covering the specimen with a non-metallic material at an area other than an area where initiation of the intergranular stress corrosion cracking is intended. Further, the tenth aspect of the present invention is characterized in that the non-metallic material is a silicone rubber or fluororubber. It is, therefore, possible to specifically limit an area of the specimen for the initiation of IGSCC as desired.

The eleventh aspect of the present invention is characterized in that the specimen has a weld, and the weld is composed of a nickel-base alloy or stainless steel. It is, therefore, possible to more surely cause only IGSCC to initiate on the specimen.

The twelfth aspect of the present invention facilitates the initiation and growth of IGSCC by controlling the stabilization parameter of the specimen to 12 or smaller.

The thirteenth aspect of the present invention applies heat treatment to the specimen to bring the specimen into a sensitized state before causing the intergranular stress corrosion cracking to initiate in the specimen. Therefore, the initiation and growth of IGSCC are facilitated.

The fourteenth aspect of the present invention specifies the temperature range and time range of heat treatment to the specimen. Accordingly, the initiation and growth of IGSCC are facilitated further.

The fifteenth aspect of the present invention is characterized in that the specimen has a weld, and the weld is composed of a ferrite-containing austenite stainless steel. It is, therefore, possible to more surely cause only IGSCC to initiate in the specimen.

The sixteenth aspect of the present invention is characterized in that the specimen has a weld, a surface of a weld bead of the weld is ground at an area thereof where initiation of intergranular stress corrosion cracking is intended, and the solution of the tetrathionate salt is brought into contact with the thus-ground surface. It is, therefore, possible to specifically limit an IGSCC initiation area of the specimen as desired, and moreover, to cause IGSCC to initiate even when the specifically-limited area is very small.

The seventeenth aspect of the present invention is characterized in that a dam is formed on the specimen in a vicinity of an area where initiation of intergranular stress corrosion cracking is intended, and the solution of the tetrathionate salt is poured into the dam to cause the intergranular stress corrosion cracking to initiate and grow in or around the weld. It is, therefore, possible to conveniently apply the test to large equipment such as actual equipment.

The eighteenth aspect of the present invention is characterized in that the specimen is a welded structure in a nuclear power plant or a simulated specimen of the welded structure, or a cut-out specimen cut out from the welded structure or the simulated specimen. It is, therefore, possible to determine the soundness or the like of materials of equipment such as reactors, in-core structures and weld zones in nuclear power plants.

The invention claimed is:

1. A method for causing intergranular stress corrosion cracking to initiate and grow in a specimen made of a material capable of retaining corrosion resistance through passivation, which comprises bringing said specimen into contact with a solution of a tetrathionate salt while applying a strain to said specimen, such that said intergranular stress corrosion cracking initiates and grows in said specimen, wherein said solution of a tetrathionate salt is an aqueous solution of potassium tetrathionate or of sodium tetrathionate, containing chlorine in a range of from 0.06 to 6 wt. % with a concentration of from 0.3 to 6 wt. % tetrathionate salt, a temperature of from 5 to 60° C., and a pH of from 3 to 6.

2. A method according to claim 1, further comprising covering said specimen with a non-metallic material at an area other than an area where initiation of said intergranular stress corrosion cracking is intended.

3. A method according to claim 1, wherein said specimen has a weld, and said weld is composed of a nickel-base alloy or stainless steel.

4. A method according to claim 1, further comprising applying heat treatment to said specimen to bring said specimen into a sensitized state before causing said intergranular stress corrosion cracking to initiate in said specimen.

* * * * *